United States Patent
Chu et al.

(10) Patent No.: US 6,307,070 B1
(45) Date of Patent: Oct. 23, 2001

(54) SUBSTITUTED AURONE DERIVATIVES

(75) Inventors: Wai-Lam Alex Chu, Shrewsbury, MA (US); Flemming R. Jensen; Thomas B. Jensen, both of Copenhagen (DK); James B. McAlpine, Bolton, MA (US); Birgitte Søkilde, Værløse; Alexandra M. SantAna-Sørensen, Gentofte, both of (DK); Sunil Ratnayake, Brea, CA (US); Jack B. Jiang, Sudbury, MA (US); Catharine Noble, Sheffield; Angela M. Stafford, Hope Valley, both of (GB)

(73) Assignee: Phytera, Inc., Worcester, MA (US)

( * ) Notice: Subject to any disclaimer, the term of this patent is extended or adjusted under 35 U.S.C. 154(b) by 0 days.

(21) Appl. No.: 09/122,257

(22) Filed: Jul. 24, 1998

Related U.S. Application Data

(63) Continuation-in-part of application No. 08/768,320, filed on Dec. 17, 1996, now abandoned, which is a continuation-in-part of application No. 08/592,793, filed on Jan. 26, 1996, now abandoned.
(60) Provisional application No. 60/053,742, filed on Jul. 25, 1997.

(51) Int. Cl.[7] .................................................. C07D 307/83
(52) U.S. Cl. ............................................. 549/466; 549/52
(58) Field of Search ....................................... 549/466, 52

(56) References Cited

U.S. PATENT DOCUMENTS

| Re. 32,196 | 7/1986 | Baker et al. | 514/382 |
|---|---|---|---|
| 3,716,531 | 2/1973 | Albrecht et al. | 549/466 |
| 3,975,380 | 8/1976 | Snader et al. | 549/466 |
| 4,067,993 | 1/1978 | Scherrer | 514/469 |
| 4,806,660 | 2/1989 | Wu | 549/466 |

OTHER PUBLICATIONS

Pare et al, Phytochemistry, vol. 30(4), p.1133–1135, 1991.*
Malhotra et al, Phytochemistry, vol. 43 (6), p. 1271–1276, Nov. 19, 1996.*
Shriner et al, J. Am. Chem. Soc., vol. 60, p. 1415–1417, 1938.*
An et al, Gazz. Chim. Ital. vol. 120 (6), p. 383–385, 1990.*
Nakatani et al, J. Org. Chem., vol. 59, p. 4360–4361, 1994.*
Chem. Abs., vol. 55, 26802e, 1961.*

* cited by examiner

Primary Examiner—Bernard Dentz
(74) Attorney, Agent, or Firm—Clark & Elbing, LLP

(57) ABSTRACT

A method for treating a fungal infection is disclosed. The method includes administering to a patient a pharmaceutical composition containing a compound of formula (IA):

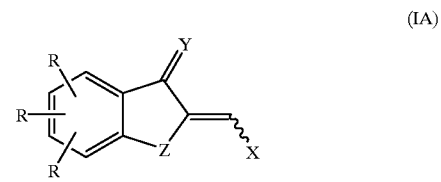

where each R is independently H, OH, Br, Cl, I, amino, thiol, nitro, $C_{1-4}$ alkoxy, $C_{1-4}$ alkenyloxy, $C_{2-6}$ alkoxyalkyleneoxy, $C_{1-4}$ alkylthio, $C_{3-18}$ alkyl, or $C_{3-18}$ alkenyl; or two adjacent R's, taken together, are a $C_{2-18}$ bivalent moiety containing at least one oxgen atom, substituted or disubstituted with A or B or both, A being H, OH, Br, Cl, I, amino, or thiol, and B being H, $C_{1-10}$ alkyl, $C_{2-18}$ alkenyl, or $C_{6-18}$ aryl; provided at least two Rs are not H;

X is $C_{4-10}$ alkyl, $C_{4-20}$ alkenyl, or a $C_{4-20}$ single, $C_{6-20}$ bridged, or $C_{6-20}$ fused ring moiety containing cycloalkyl, cycloalkenyl, aryl, heterocycle, or heteroaryl, where X is substituted with H, OH, Cl, Br, I, amino, cyano, nitro, alkyl, alkoxy, alkenyl, or alkenyloxy; provided that if X is a heteroaryl or heterocyclic moiety where two Rs are each OH and meta to each other, then the remaining R is H and ortho to each of the two hydroxyls, and Y and Z are each O and a ring atom of X is linked directly to the $sp^2$ carbon atom adjacent to X, then substituted with H, OH, Cl, Br, I, amino, cyano, alkyl, alkoxy, alkenyl, or alkenyloxy; and each of Y and Z is independently selected from O, S, and NH; or a pharmaceutically acceptable salt or ester thereof.

6 Claims, No Drawings

SUBSTITUTED AURONE DERIVATIVES

CROSS REFERENCE TO RELATED APPLICATIONS

This application is a continuation-in-part of application U.S. Ser. No. 08/768,320, filed Dec. 17, 1996, now abandoned which in turn is a continuation-in-part of application U.S. Ser. No. 08/592,793, filed Jan. 26, 1996. now abandoned This application claims priority from provisional application U.S. Ser. No. 60/053,742, filed Jul. 25, 1997.

BACKGROUND OF THE INVENTION

The invention relates to substituted aurone derivatives and to methods of inhibiting microbial infections with substituted aurone derivatives.

Microbial infections, such as fungal infections and bacterial infections, can contribute to and complicate many diseases, including meningitis, pulmonary diseases, and respiratory tract diseases. Opportunistic infections have proliferated, particularly in immunocompromised patients, such as those with AIDS, those undergoing chemotherapy for cancer, and those undergoing therapy to prevent graft rejection following organ transplant surgery.

Fungal infections (mycoses) may be cutaneous, subcutaneous, or systemic. Superficial mycoses include tinea capitis, tinea corporis, tinea pedis, onychomycosis, perionychomycosis, pityriasis versicolor, oral thrush, and other candidoses such as vaginal, respiratory tract, biliary, esophageal, and urinary tract candidoses. Systemic mycoses include systemic and mucocutaneous candidosis, cryptococcosis, aspergillosis, mucormycosis, paracoccidioidomycosis, North American blastomycosis, histoplasmosis, coccidioidomycosis, and sporotrichosis.

Pathogenic organisms include dermatophytes (e.g., Microsporum canis and other M. spp.; and Trichophyton spp. such as *T. rubrum*, and *T. mentagrophytes*), yeasts (e.g., *Candida albicans* or *C. tropicalis*), *Torulopsis glabrata, Epidermophyton floccosum, Malassezia furfur (Pityropsporoti orbictilare,* or *P. ovale), Cryptococcus neoformans, Aspergillus fumigatus* and other Aspergillus spp., Zygomycetes (e.g., Rhizopus, Mucor), *Paracoccidiodes brasiliensis, Blastomyces dermatitidis, Histoplasma captuslatum, Coccidioides immitis,* and *Sporothrix schenckii*.

SUMMARY OF THE INVENTION

In one aspect, the invention features a method for treating a microbial infection. The method includes administering to a patient a pharmaceutical composition containing a compound of formula (IA):

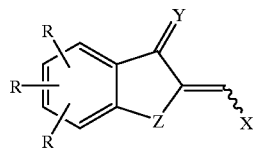

(IA)

where
each R is independently H, OH, Br, Cl, I, amino, thoil, nitro, $C_{1-4}$ alkoxy, $C_{1-4}$ alkenyloxy, $C_{2-6}$ alkoxyalkyleneoxv, $C_{1-4}$ alkylthio, $C_{3-18}$ alkyl, or $C_{3-18}$ alkenyl; or two adjacent Rs, taken together, are a $C_{2-18}$ bivalent moiety containing at least one oxgen atom, substituted or disubstituted with A or B, or both, A being H, OH, Br, Cl, I, amino, or thiol, and B being H, $C_{1-10}$ alkyl, $C_{2-18}$ alkenyl, or $C_{6-18}$ aryl; provided at least two Rs are not H;

X is $C_{4-10}$ alkyl, $C_{4-20}$ alkenyl, or a $C_{4-20}$ single, $C_{6-20}$ bridged, or $C_{6-20}$ fused ring moiety containing cycloalkyl, cycloalkenyl, aryl, heterocycle, or heteroaryl, where X is substituted with H, OH, Cl, Br, I, amino, cyano, nitro, alkyl, alkoxy, alkenyl, or alkenyloxy; provided that if X is a heteroaryl or heterocyclic moiety where two of R are each OH and meta to each other, the remaining R is H and ortho to each of the two hydroxyls, Y and Z are each O, and a ring atom of X is linked directly to the $sp^2$ carbon atom adjacent to X, then substituted with H, OH, Cl, Br, I, amino, cyano, alkyl, alkoxy, alkenyl, or alkenyloxy; and each of Y and Z is independently selected from O, S, and NH; or a pharmaceutically acceptable salt or ester thereof.

In another aspect, the invention provides a compound selected from formulae (I)–(IV) below:

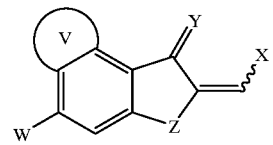

(I)

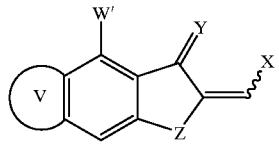

(II)

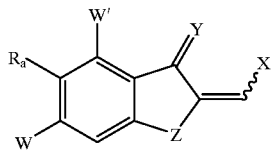

(III)

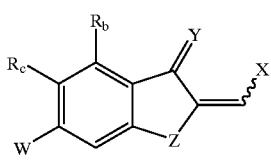

(IV)

where
V is a bivalent $C_{2-18}$ moiety containing at least one oxygen atom and substituted with A, B, or both;
each of W and W' is independently selected from the values for A, cyano, nitro, $C_{1-4}$ alkoxy, $C_{1-4}$ alkenyloxy, $C_{2-6}$ alkyloxyalkyleneoxy, $C_{2-7}$ carboxyalkyloxy, $C_{7-15}$ arylalkoxy, and $C_{1-4}$ alkylthio;
$R_a$ is H, $C_{3-18}$ alkyl, $C_{3-18}$ alkenyl, $C_{5-18}$ cyclohexenyl, $C_{6-18}$ aryl;
each of $R_b$ and $R_a$ is independently selected from H and $C_{1-4}$ alkyl;
X is substituted or unsubstituted $C_{3-15}$ alkyl $C_{3-18}$ alkenyl, $C_{3-15}$ cycloalkyl, $C_{4-15}$ cycloalkenyl, $C_{4-20}$ bicyclo [a.b.c]alkyl, $C_{5-20}$ bicyclo[a.b.c] alkenyl, $C_{8-20}$ tricyclo [a.b.c.d]alkyl, $C_{8-20}$ tricycloalkenyl, $C_{2-20}$ heterobicyclo[a.b.c]alkyl, or a combination thereof, where each of a, b, c, and d is independently 0 to 10 (e.g., 0 to 4, 0 to 6, or 1 to 7); and each of Y and Z is independently selected from O and S.

In another aspect, the invention features compounds of the formulae below:

(V)

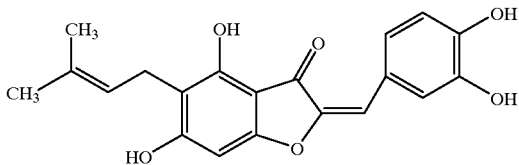

(VI)

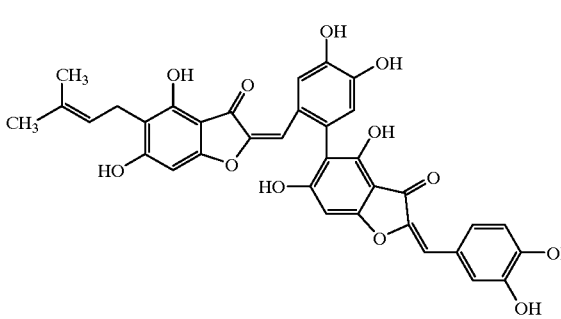

The invention also features synthetic methods suitable for combinatorial synthetic strategies for the production of diverse libraries of structurally related compounds. Other features and advantages of the invention will be apparent from the following detailed description, and from the claims.

DETAILED DESCRIPTION

In one aspect, the invention features a method of inhibiting a microbial infection, where the compound of formula (IA) is selected from formulae (I)–(IV):

(I)

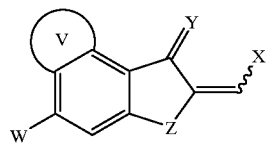

(II)

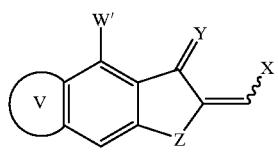

(III)

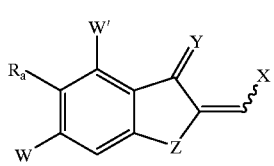

-continued (IV)

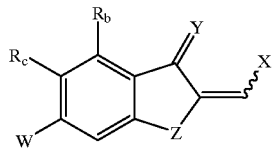

In one aspect, V is a bivalent $C_{2-18}$ moiety containing at least one oxygen atom and substituted with A, B, or both. V can contain between 1 and 3 rings, e.g., 1 ring, 2 rings, or three rings. For example, V can be selected from the following five formulae:

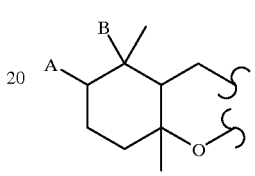

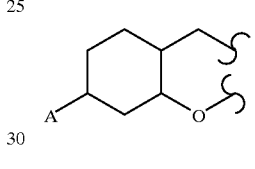

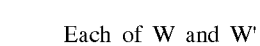

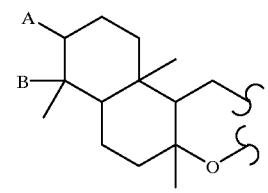

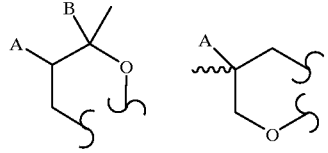

Each of W and W' is independently selected from the values for A, cyano, nitro, $C_{1-4}$ alkoxy, $C_{1-4}$ alkenyloxy. $C_{2-6}$ alkyloxyalkyleneoxy, $C_{2-7}$ carboxyalkyloxy, $C_{7-15}$ arylalkoxy, and $C_{1-4}$ alkylthio.

$R_a$ is H, $C_{3-18}$ alkyl, $C_{3-18}$ alkenyl, $C_{5-18}$ cycohexenyl, or $C_{6-18}$ aryl. For example, $R_a$ is H, prop-2-enyl, cinnamyl, 2-methylprop-2-enyl, but-2-enyl, 3-methylbut-2-enyl, 3,7-dimethylocta-2,6-dienyl, (cyclohexenyl)methyl, 3,7,11-trimethyldodeca-2,6,10-trienyl, or benzyl. In some cases, $R_a$ is not prenyl or isoprenyl.

Each of $R_b$ and $R_c$ is independently selected from H and $C_{1-4}$ alkyl. In one method, the compound can be of the formula Q=(CHX) where Q is derived from the benzofuranone analogs or derivatives in from Schemes Q-1 through Q-11, and the geometry of the double bond is E or Z. In Schemes Q-1 through Q-11, the compounds are of the formula Q-H$_2$, where the two hydrogens are methylene hydrogens.

In another aspect, the compound has an IC$_{50}$ of less than 50 micrograms per milliliter against at least one pathogenic strain of Candida or Aspergillus.

In another aspect, a compound is of formula (III), where each of Y and Z is independently selected from O and S, for example, formulae S01–S06 and S08–S19 of Scheme P-1. Other embodiments include a compound where: W and W' are independently selected from H, OH, methoxy, methoxymethyleneoxy, and carboxymethoxy; where Y and Z are O, and at least one of W and W' is OH; where X is a heterocyclic radical, e.g., a heteroaryl; where X is $C_{4-10}$ alkyl, $C_{4-20}$ alkenyl, or a $C_{4-20}$ single, $C_{6-20}$ bridged, or $C_{6-20}$ fused ring moiety containing cycloalkyl, cycloalkenyl, or aryl; where X is a nonaromatic moiety containing cycloalkyl, cycloalkenyl, alkyl, or alkenyl; or where the compound is selected from S12 and S02.

Examples of X include benzyl, 2,5-dimethoxyphenyl, 2,3-dimethyl-4-methoxyphenyl, 3-benzyloxyphenyl, 3-phenoxyphenyl, 4-benzyloxy-3-methoxyphenyl, 4-[3-propenoic acid]-phenyl, 2-ethoxy-1-naphthyl, 1-(methylthio)ethyl, DL-1-phenylethyl, 4-n-pentyloxyphenyl, 1-(phenylsulfonyl)-2-pyrrolyl, 4-(3-dimethylaminopropoxy)phenyl, 3-phenylpropyl, 2,4-diethoxy-m-tolulyl, 2,6,6-trimethylcyclohexene-1-methyl, 2,5-dimethoxy-3-tetrahydrofuranyl, 4-methyl-5-imidazolyl, 4-n-pentylphenyl, 2-benzyloxy-4,5-dimethoxyphenyl, 1-pyrenyl, 3,5-dibenzyloxy-3-methoxyphenyl, 3-methyl-4-methoxyphenyl, 4-n-decyloxyphenyl, 2,4-dimethoxy-3-methylphenyl, t-butyl, 3-(4-t-butylphenoxy)phenyl, 2-n-hexyloxyphenyl, 2-(4-chlorophenylthio)phenyl, cyclopropyl, 2,6-dimethoxy-4-hydroxyphenyl, 4-benzyloxyphenyl, 2-benzyloxyphenyl, 8-hydroxy-1,1,7,7-tetramethyljulolidin-9-yl, 2,3,6,7-tetrahydro-8-hydroxyjulolidin-9-yl, 2-methoxymethyl-1-pyrrolidinyl, 5-(2-nitrophenyl)furanyl, 1,1-dimethyl-2-hydroxyethyl, 5-methylfuranyl, 5-(3-chlorophenyl)furanyl, 2,4-hexadienyl, 5-[3(trifluoromethyl)-phenylfuranyl], 4,5-dimethyl-4-pentenyl, imidazolyl, ferrocenyl, 2,6-dimethylhept-5-enyl, 5-[2-(trifluoromethyl)-phenyl] furanyl, 5-(hydroxy-2-nitromethyl)furanyl, 2,4-dimethyl-2,6-heptadienyl, 1-phenylethyl, 5-(2-chlorophenyl)furanyl, benzyl, 5-ethyl-2-furanyl, 5-(4-nitrophenyl)-furanyl, pentamethylphenyl, 1-(methyldithio)isopropyl 4-trifluoromethylphenyl, 3-fluoro-4-methoxyphenyl, or the of a compound of Schemes X-1 through X-10, where the compounds of Schemes X-1 through X-10 have the formulae X-CHO.

The fungal infection can be: an infection of a Candida species an infection of a fungus resistant to at least one azole antifungal agent (e.g., where the azole antifungal agent is fluconazole); or an infection of an Aspergillits species. Examples of pathogen strains include *C. albicans, C. glabrata, C. krusei, C. tropicalis, C. parapsilosis, A. fumigatus,* and *A. niger.*

The invention also features aurone derivatives, such as those described in formulae (I)–(IV) in the Summary section. Examples of these compounds include those where X is $C_{3-15}$ alkyl, $C_{3-18}$ alkenyl, $C_{3-15}$ cycloalkyl, $C_{4-15}$ cycloalkenyl, $C_{5-10}$ bicyclo[a.b.c]alkyl, $C_{5-10}$ bicyclo[a.b.c] alkenyl, $C_{8-20}$ tricyclo[a.b.c.d]alkyl, $C_{8-20}$ tricycloalkenyl, $C_{3-10}$ heterobicyclo[a.b.c]alkyl, or a combination thereof, where each of a, b, c, and d is independently 0 to 6; X is $C_{3-15}$ alkyl, $C_{3-18}$ alkenyl, $C_{3-15}$ cycloalkyl, or $C_{4-15}$ cycloalkenyl; where X is $C_{5-10}$ bicvclo[a.b.c.]alkyl, $C_{5-10}$ bicyclo[a.b.c]alkenyl, $C_{8-15}$ tricyclo[a.b.c.d] alkyl, $C_{8-15}$ tricycloalkenyl, $C_{3-10}$ heterobicyclo[a.b.c]alkyl, or a combination thereof; where W and W' are each independently selected from H, hydroxyl, methoxy, hydroxymethyl, and halomethyl; and where W and W' are each hydroxyl; or a combination thereof. The bridges can be ortho-fused or ortho- and peri-fused. The bridge can be alkylene, azo, azimino, biimino, epidioxy, nitrilo, imino, furano, epoxythioxy, epithio, alkanoxy, epoxy, or alkanoxyalkano (e.g., methanoxymethano). The invention also features additional novel compounds described in the above method of treatment, including the compounds shown below.

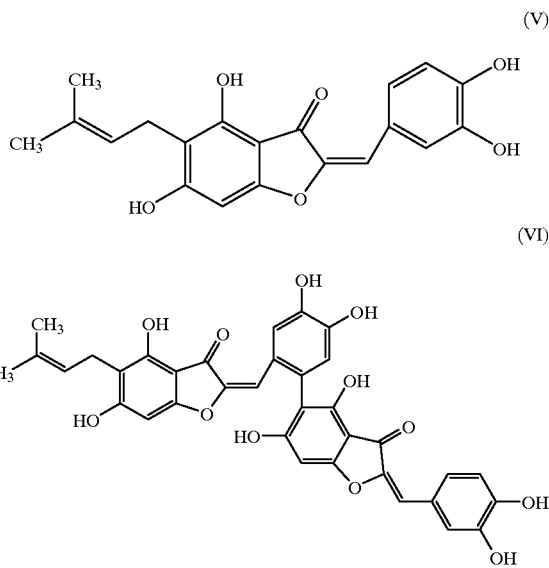

In some embodimentsl enantiomers of disclosed compounds are separated. The bridging olefinic bond between Q and X is sometimes preferably E (entgegen) and sometimes preferably Z (zusamnien). Depending on the individual embodiment, chiral centers may be (R) or (S).

Terms

Some terms are defined below, and some terms are defined elsewhere in the disclosure.

Alkyls may be substituted or unsubstituted and may be straight, branched, or cyclic. Preferably, alkyl groups hav-e between 1 and 10 carbon atoms, and more preferably have between 1 and 6 carbon atoms. Examples of alkyls include methyl, ethyl, propyl, isopropyl, butyl, isobutyll sec-butyl, t-butyl, pentyl, cyclopentyl, isopentyl, neopentyl, t-pentyl, sec-pentyl, hexyl, cyclohexyl, isohexyl, 2,3-dimethylbutyl, 2,2-dimethylbutyl, 3-ethylpentyl, 3,4-dimethylpentyl, heptyl, octyl, nonyl, decyl, and (2,3,4-trimethylcyclo-hexyl) methyl. An alkylene is a bivatent hydrocarbon, e.g., an alkyl group with an additional hydrogen removed, such as methylene, propylene, or 1,4-cyclohexylene. Alkoxy groups are alkyl groups linked to the remainder of the molecule, e.g., a ring, by an oxygen. Alkoxy groups also include polyethers, such as methoxyethyloxy. Alkyl, alkenyl, alkynyl, aryl, and heterocyclic radicals, whether or not substituting groups, (discussed below) may be linked by alkyl, alkenyl, alkynyl, ether, ester, amide, urea, urethane, amino, thioether, or thioester groups, such as methoxymethyl and alkylthioalkyl.

Alkenyls are alkyl groups with one or more unsaturated carbon-carbon bonds, such as cyclopentenyl, cyclopentadienyl, cyclohexadiene, but-2-enyl, 3,4-dimethylpent-3-enyl, allyl, vinyl, prenyl, isoprenyl, and norbornenyl. Examples of alkenylenes include vinylene and propenylene. Similarly, alkynyl groups have one or more triple bonds, and may also include one or more double bonds.

Aryls include aromatic rings, substituted or unsubstituted, preferably having between 6 and 20 carbon atoms, and more preferably between 6 and 14 carbon atoms, exclusive of substitution on the ring. Examples of aryls include phenyl, naphthyl, indenyl, pentalenyl, anthryl, azulyl, and biphenylyl. Combinations include alkylaryls (e.g., tolyl, xylyl, mesityl, cumenyl, 2-ethyl-4 methylphenyl) and arylalkyls (e.g., benzyl, phenylethyl,) or arylalkenyls, and divalent arylenes such as 1,4-phenylene.

Haloalkyl (or haloalkenyl or haloalkynyl) includes any alkyl (or alkenyl or alkynyl) group where at least one hydrogen is replaced with a halogen (fluorine, chlorine, bromine, or iodine). Where more than one hydrogen is replaced (e.g., a dihaloalkyl or a hexahaloalkyl), the halogens are selected independently and may be on the same carbon atom or on different carbon atoms. Amino-substituted, nitro-substituted, or otherwise substituted alkyls (or alkenyls or alkynyl or aryls) are analogous to the above. Halomethyls include perchloromethyl, bromomethyl, and fluorochloromethyl.

Heterocyclic radicals may be aromatic (heteroaryl) or nonaromatic, and substituted or unsubstituted. They have one, two or three rings which are single, fused, bridged rings, or polycyclic. They contain between 2 and 15 carbon atoms in the ring, i.e., exclusive of substitution. They can be linked to the rest of the molecule through a carbon atom or a heteroatom. Heterocyclic radicals include thienyl, thianthrenyl, furanyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, pyridyl, pyrazinyl, pyrimidinyl, pyridazinyl, indolizinyl, isoindolyl, quinuclidinyl, 3H-indolyl, indolyl, indazolyl, purinyl, 4H-quinolizinyl, isoquinolyl, quinolyl, phthalazinyl, naphthyridinyl, quinoxalinyl, cinnolinyl, pteridinyl, 4H-carbazolyl, carbazolyl, beta-carbolinyl, phenanthridinyl, acridinyl, perimidinyl, phenanthrolinyl, phenazinyl, phenothiazinyl, phenoxazinyl, isochromanyl, chromanyl, furazanyl, pyrrolinyl, pyrrolidinyl, imidazolidinyl, pyrazolidinyl, pyrazolinyl, imidazolinyl, piperidyl, piperazinyl, and morpholinyl. Heterocyclic radicals also include benz[h]isoquinolinyl, thieno[2,3-b]furanyl, 2H-furo[3,2-b]pyranyl.

Substituted moieties have one, two, three, or more of the following independently selected substituting moieties (instead of a hydrogen): $C_{1-10}$ alkyl, $C_{2-10}$ alkenyl, $C_{1-10}$ alkoxy, $C_{2-10}$ alkenyloxy, $C_{1-10}$ haloalkyl, $C_{1-10}$ haloalkoxy, aryl, aryloxy, hydroxy, nitro, chloro, fluoro, bromo, and iodo, thiol, cyano, and amino. Substituting moieties also include combinations of the above with carbonyl (acyl), sulfonyl, thionyl (e.g., thioketone), and carboxyl, such as alkyloxycarbonyl, arylalkyloxy, (N,N-dialkylamino)alkoxy, arylsulfonyl, and carboxylic acids. In some embodiments, substituting moieties have between 1 and 6 carbon atoms, and more preferably have between 1 and 3 carbon atoms. Examples of carbon-containing substituting moieties include chloromethyl, hydroxymethyl, bromoethyl, methoxy, and ethoxy. An alkyl does not have an alkyl or haloalkyl substituent, although, for example, a cycloalkyl may have an alkyl or haloalkyl substituent.

The invention also encompasses compounds identical to any of the disclosed structures (e.g., formula (IV) or formula (V)), except that one or more conventional protecting groups are used, such as hydroxyl protecting groups, carboxylate protecting groups, and carbonyl protecting groups. Methods of adding and removing such protecting groups are well known in the art (see, for example, *Protective Groups in Organic Synthesis*, by T. W. Greene and P. G. M. Wuts, 2nd ed., 1991, Chapters 2–5).

For example, the following representative hydroxyl protecting groups are provided. There is some overlap between the above-described R moieties and the disclosed hydroxyl protecting groups.

Methyl ethers include methoxymethyl; methylthiomethyl; t-butylthio-methyl; (phenyldimethyldiyl)methoxy-methyl; benzyloxymethyl; p-methoxybenzyl-oxymethyl; (4-methoxyphenoxy)methyl; guaiacolmethyl; t-butoxymethyl; 4-pentenyloxymethyl; siloxymethyl; 2-methoxyethoxymethyl; 2,2,2-trichloro-ethoxymethyl; bis(2-chloroethoxy)methyl; 2-(trimethylsilyl)ethoxymethyl; tetrahydropyran-2-yl; 3-bromotetrahydropyran-2-yl; 1-methoxycyclohexyl; 4-methoxy-tetrahydropyran-2-yl; 4-methoxytetrahydrothiopyran-2-yl; 4-methoxytetrahydrothio-pyran-2-yl-S,S-dioxido; 1-[(2-chloro-4-methyl)phenyl]-4-methoxypiperidin-4-yl; 1,4-dioxan-2-yl; tetrahydrofuranyl; tetrahydrothiofuranyl; and 2,3,3a,4,5,6,7,7a-octahydro-7,8,8-trimethyl-4,7-methanobenzofuran-2-yl.

Ethyl ethers include 1-ethoxyethyl; 1-(2-chloroethoxy)ethyl; 1-methyl-1-methoxyethyl; 1-methyl-i -benzyloxy-2-fluoroethyl; 2,2,2-trichloroethyl; 2-trimethylsilylethyl; 2-(phenylselenyl)ethyl; t-butyl; allyl; p-chlorophenyl; p-methoxyphenyl; and 2,4-dinitrophenyl.

Benzyl ethers include benzyl; p-methoxybenzyl; 3,4-dimethoxybenzyl; o-nitrobenzyl; p-nitrobenzyl; p-halobenzyl; 2,6-dichlorobenzyl; p-cyanobenzyl; p-phenylbenzyl; 2- and 4-picolyl; 3-methyl-2-picolyl-N-oxido; diphenylmethyl; p,p'-dinitrobenzhydryl; 5-dibenzosuberyl; triphenylmethyl; a-naphthyldiphenylmethyl; p-methoxyphenyldiphenylmethyl; di(p-methoxyphenyl)phenylmethyl; tri(p-methoxyphenyl)methyl; 4-(4'-bromophenacyloxy)phenyldiphenylmethyl; 4,4'1,4"-tris(4,5-dichlorophthalimidophenyl)methyl; 4,4',4"-tris-(levulinoyloxyphenyl)methyl; 4,4',4"-tris (benzoyloxyphenyl)methyl; 3-(imidazol-1-ylmethyl)bis(4', 4"-dimethoxyphenyl)-methyl; 1,1-bis(4-methoxyphenyl)-1'-pyrenylmethyl; 9-anthryl; 9-(9-phenyl)xanthenyl; 9-(9-phenyl-10-oxo)anthryl; 1,3-benzodithiolan-2-yl; and benzisothiazolyl S,S-dioxido.

Silyl ethers include trimethylsilyl; triethylsilyl; triisopropylsilyl; dimethylisopropylsilyl; diethylisopropyl-silyl; dimethylthexylsilyl; t-butyldimethylsilyl; t-butyl-diphenylsilyl; tribenzylsilyl; tri-p-xylylsilyl; triphenyl-silyl; diphenylmethylsilyl; and t-butylmethoxyphenylsilyl.

Esters include formate; benzoylformate; acetate; chloroacetate; trichloroacetate; methoxyacetate; triphenyl-methoxyacetate; phenoxyacetate; p-chlorophenoxyacetate; p-(phosphate)phenylacetate; 3-phenylproprionate; 4-oxopentanoate (levulinate); 4,4-(ethylenedithio) pentanoate; pivaloate; adamantoate; crotonate; 4-methoxycrotonate; benzoate; p-phenylbenzoate; and 2,4, 6-trimethylbenzoate.

Carbonates include methyl carbonate; 9-fluorenyl-methylcarbonate; ethyl carbonate; 2,2,2-trichloroethyl carbonate; 2-(trimethylsilyl)ethyl carbonate; 2-(phenylsulfonyl)ethyl carbonate; 2-(triphenylphosphono) ethyl carbonate; isobutyl carbonate; vinyl carbonate; allyl carbonate; p-nitrophenyl carbonate; benzyl carbonate; p-methoxybenzyl carbonate; 3,4-dimethoxybenzyl carbonate; o-nitrobenzyl carbonate; p-nitrobenzyl carbonate; S-benzyl thiocarbonate; 4-ethoxy-1-naphthyl carbonate; and methyl dithiocarbonate.

Protecting groups with assisted cleavage include 2-iodobenzoate; 4-azidobutyrate; 4-nitro-4-methylpentanoate; o-(dibromomethyl)benzoate; 2-formylbenzenesulfonate; 2-(methylthiomethoxy)ethyl carbonate; 4-(methylthiomethoxy)-butyrate; and 2-(methylthiomethoxymethyl) benzoate.

Miscellaneous esters include 2,6-dichloro-4-methylphenoxyacetate; 2,6-dichloro-4-(1,1,3,3-tetramethylbutyl)phenoxyacetate; 2,4-bis(1,1-dimethylpropyl)-phenoxy-acetate; chlorodiphenylacetate; isobutyrate; monosuccinoate; (E)-2-methyl-2-butenoate (tigloate); o-(methoxycarbonyl)benzoate; p-benzoate; a-naphthoate; nitrate; alkyl N,N,N',N'-tetramethylphosphorodiamidate; N-phenylcarbamate; borate; dimethylphosphinothioyl; and 2,4-dinitrophenyl-sulfenate.

Sulfonates include methanesulfonate (mesylate); benzylsulfonate; and tosylate.

Cyclic acetals and ketals include methylene; ethylidene; 1-t-butylethylidene; 1-phenylethylidene; 4-methoxyphenylethylidene; 2,2,2-trichloroethylidene; acetonide (isopropylidene); cyclopentylidene; cyclohexylidene; cycloheptylidene; benzylidene; p-methoxybenzylidene; 2,4-dimethoxybenzylidene; 3,4-dimethoxybenzylidene; and 2-, 3-, or 4-nitrobenzylidene.

Cyclic ortho esters include methoxymethylene; ethoxymethylene; dimethoxymethylene; 1-methoxyethylidene; 1-ethoxyethylidine; 1,2-dimethoxyethylidene; α-methoxybenzylidene; 1-(N,N-dimethylamino)ethylidene derivative; α-(N,N-dimethylamino)benzylidene derivative; and 2-oxacyclo-pentylidene.

Note that these cyclic ortho esters, like the bivalent organic moieties recited above for adjacent pairs of substituents (e.g., $R_1$ and $R_2$ in formula (IV)), may react with non-adjacent hydroxyl moieties. For example, a bivalent organic moiety recited in the preceding paragraph or recited above for adjacent pairs of substituents may be selected for two nonadjacent substituents on the same molecule or for any two substituents on two separate molecules. The two separate molecules can be the same or different, and are selected from compounds disclosed herein.

Silyl derivatives include di-t-butylsilylene group; 1,3-(1,1,3,3-tetraisopropyldisiloxanylidene) derivative; tetra-t-butoxydisiloxane-1,3-diylidene derivative; cyclic carbonates; cyclic boronates; ethyl boronate; and phenyl boronate.

Preferred protecting groups for catechols include cyclic acetals and ketals such as methylene, acetonide, cyclohexylidene, and diphenylmethylene; and cyclic esters such as cyclic borate and cyclic carbonate.

The invention encompasses other $C_{1-10}$ hydroxyl protecting groups not individually identified above which are pharmaceutically acceptable, and are optionally metabolized (e.g., cleaved or modified) to form one of the compounds disclosed herein. In other words, the invention encompasses metabolic precursors of the disclosed compounds and metabolites of the disclosed compounds having antimicrobial activity.

The invention also encompasses amides, amine salts, and other organic salts of the disclosed compounds. Amides may be formed by reacting a disclosed compound or activated derivative thereof with any naturally-occurring amino acid, an oligopeptide having up to 10 (e.g., 4, 3, or 2) residues, a peptidomimetic having a molecular weight less than 300, or any $C_{1-20}$ organic moiety having an amino group that is not already described above. The term "naturally occurring amino acid" is meant to include the 20 common α-amino acids (Gly, Ala, Val, Leu, Ile, Ser, Thr, Asp, Asn, Lys, Glu, Gln, Arg, His, Phe, Cys, Trp, Tyr, Met and Pro), and other amino acids that are natural products, such as norleucine, ethylglycine, ornithine, methylbutenylmethylthreonine, and phenylglycine. Examples of amino acid side chains include H (glycine), methyl (alanine), —$CH_2$—(C=O)—$NH_2$ (asparagine), —$CH_2$—SH (cysteine), and —CH(OH)$CH_3$ (threonine).

Subjects or patients of the disclosed methods may be any living animal, plant, or plant product (e.g., grain or feed). Animals include mammals, particularly humans. Animals also include domestic animals bred for food or as pets, such as horses, cows, sheep, poultry, fish, pigs, cats, dogs, and zoo animals. Plants include trees, crops, grasses, and flowering plants.

SCHEME A

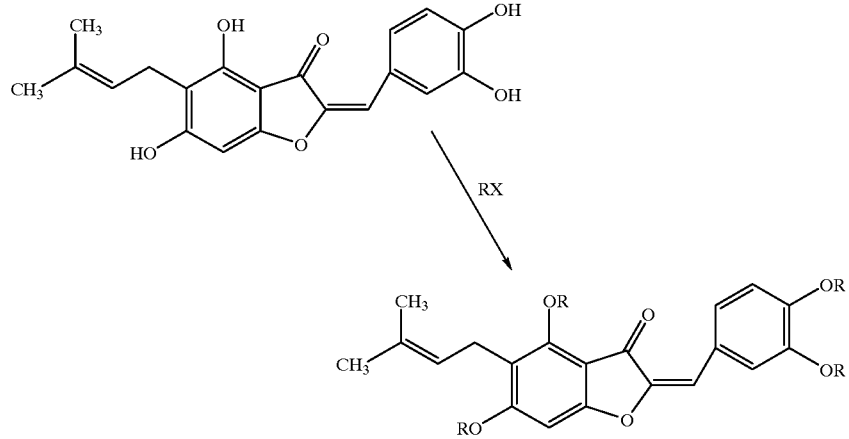

-continued
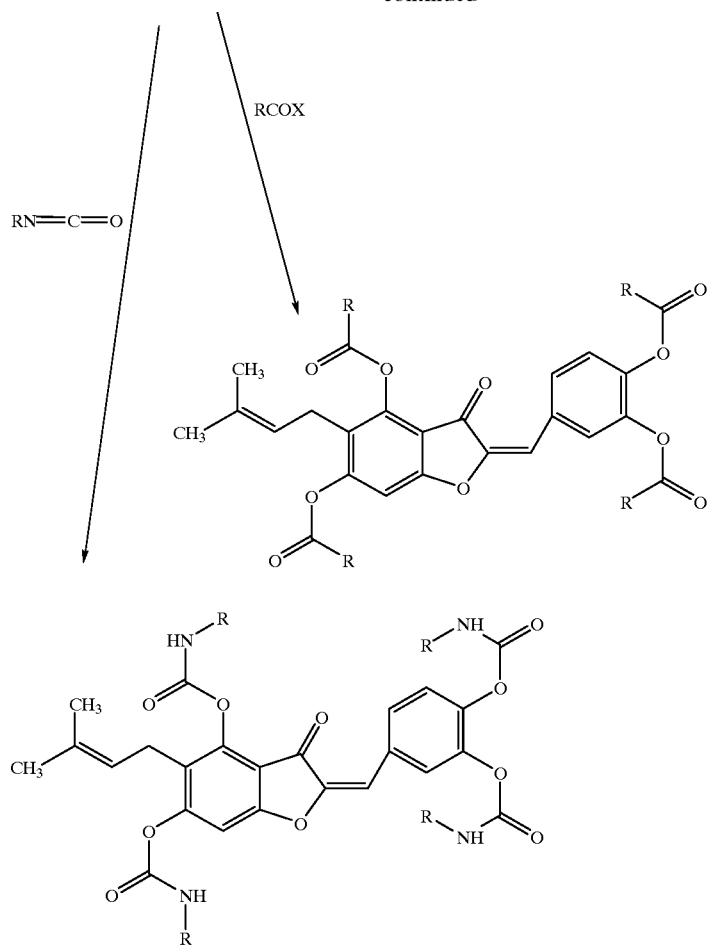
SCHEME B
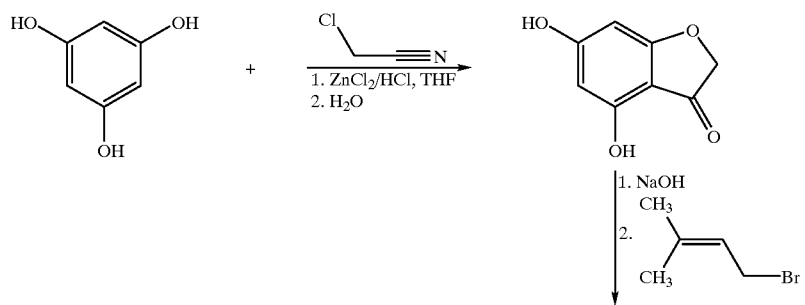

-continued
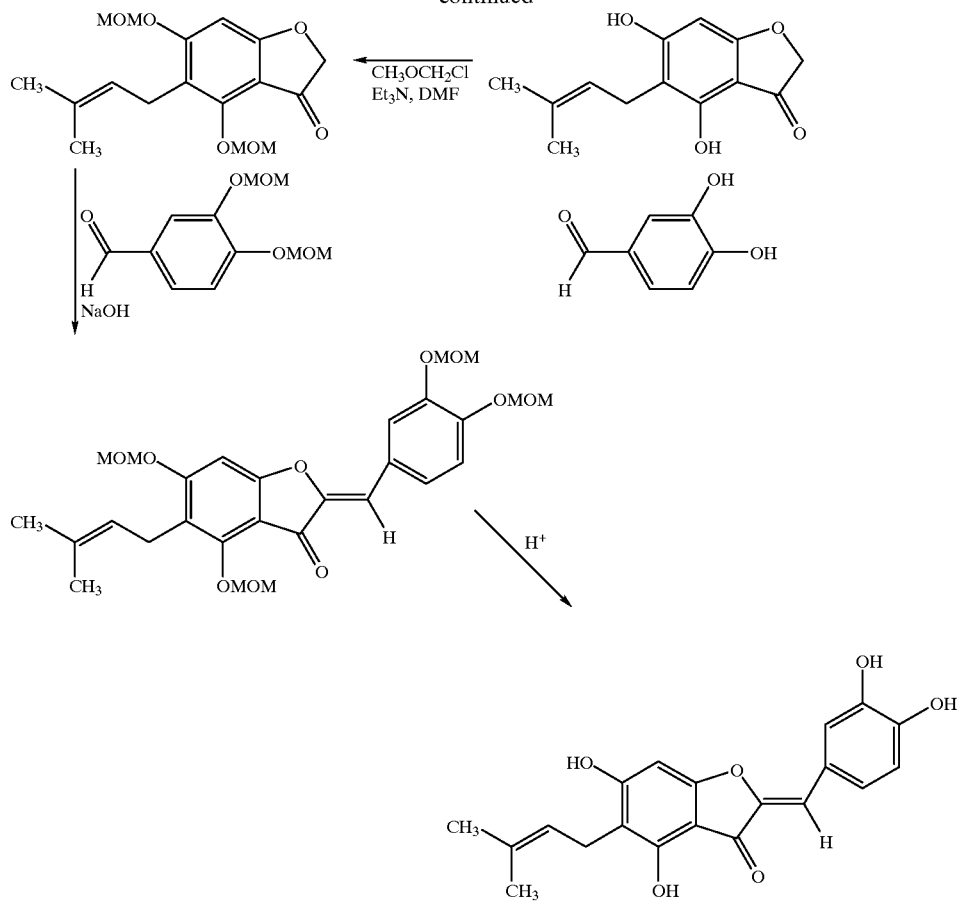
SCHEME C
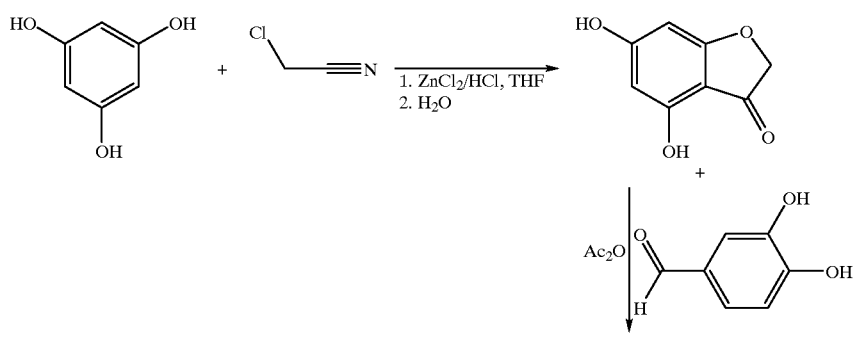

-continued

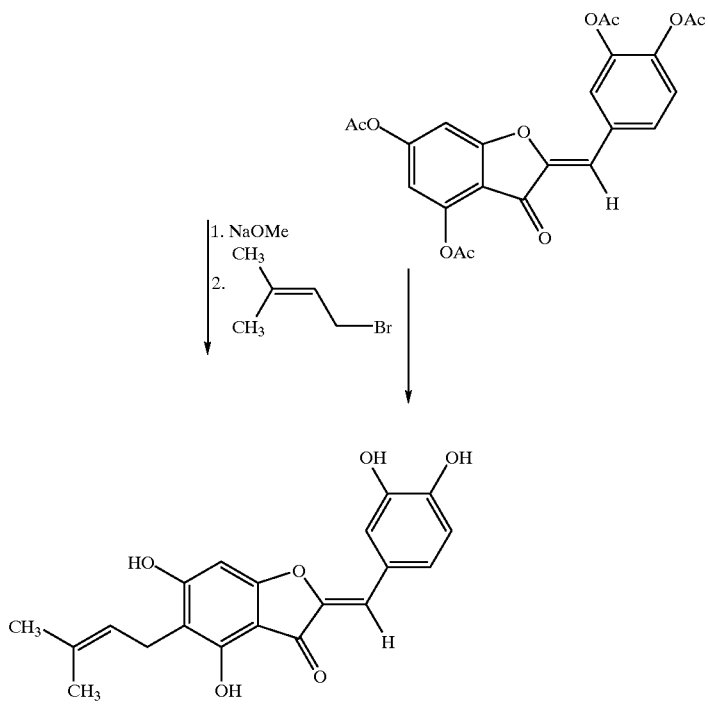

Synthesis

The compounds of formula (V) and (VI) can be isolated from plant cultures of *Ficus religiosa* (Examples 13 and 14). The compounds of the invention can also be synthesized using techniques known to one of skill in the art. For example, the compound (V) can be made as described in Schemes B and C, and in Examples 15 to 20. Using this compounds as a starting material, the disclosed derivatives can be prepared by semi-synthetic routes (see representative Scheme A based on formula (V)).

For example, phenolic hydroxy groups are etherified in the presence of a base or a dehydrating agent (Scheme A). Examples of bases include alkali metal hydroxides such as sodium hydroxide or carbonates such as potassium carbonate. Dehydrating agents include dicyclohexylcarbodiimide, lower alkanols (such as pentanol or ethanol), dialkylsulfates (such as dimethylsulfate), and alkyl halides (such as butyl bromide). Etherifications may require heating in solvents such as dichloroethane, methoxyethylether, or dimethylformamide. Alternatively, treatment of phenolic hydroxyl groups with triethylsilane and an aldehyde or ketone in the presence of a strong acid produces ethers via formation of a hemiacetal and reduction of the hydroxyl (Doyle, et al., *J. Am. Chem. Soc.* 94:3659 1972). Use of a ketone produces branched alkyl ethers such as isopropyl ethers.

Phenolic hydroxy groups are esterified with acylating agents such as optionally substituted alkane carboxylic or sulfonic acids, anhydrides, acid halides (e.g., acetylchloride, methylsulfonyl chloride, and tosyl chloride), or hydrohalic acids (e.g., reactive esters such as thionyl chloride and phosphorous tribromide) (Scheme A). These esterifications are generally carried out at room temperature and can require cooling in an inert solvent such as tetrahydrofuran or dichloromethane. A base (aqueous alkali or a nucleophilic base such as pyridine or 4-(N,N-dimethylamino)pyridine) can be added in reactions with acid halides; nucleophilic bases are used in reactions with anhydrides. For hindered acids or tertiary R, the alkoxide can be substituted for the alcohol (phenol) (Kaiser and Woodruff, *J. Org. Chem.* 35:1198 (1970)) Thallium salts of phenols (Taylor, McLay, and McKillop, *J. Am. Chem. Soc.* 90:2422 (1968)), and phase transfer catalysis (Illi, *Tetrahedron. Lett.* 2431 (1979)) can be used for hindered phenols.

Carbamates are formed by reacting phenolic hydroxy groups with alkyl isocyanates in solvents such as DMSO, DMF, THF or halogenated hydrocarbons at temperatures between room temperature and solvent reflux (Scheme A). Replacing the alkyl isocyanate with cyanic acid gives unsubstituted carbamates; replacing the alkyl isocyanate with isothiocyanate gives the thiocarbamate, although this reaction occurs more slowly than the isocyanate reaction. Formation of carbamates can be catalyzed by organometallic compounds (*J. Chem. Soc. C.* 2663 (1967), 1479 (1968)), or by light (*J. Org. Chem.* 42:1428 (1977)). The above-described transformations are also applicable to formulae (III), (VI), and (VIII) for the preparation of analogous derivatives (e.g., Scheme A).

Scheme Q-1
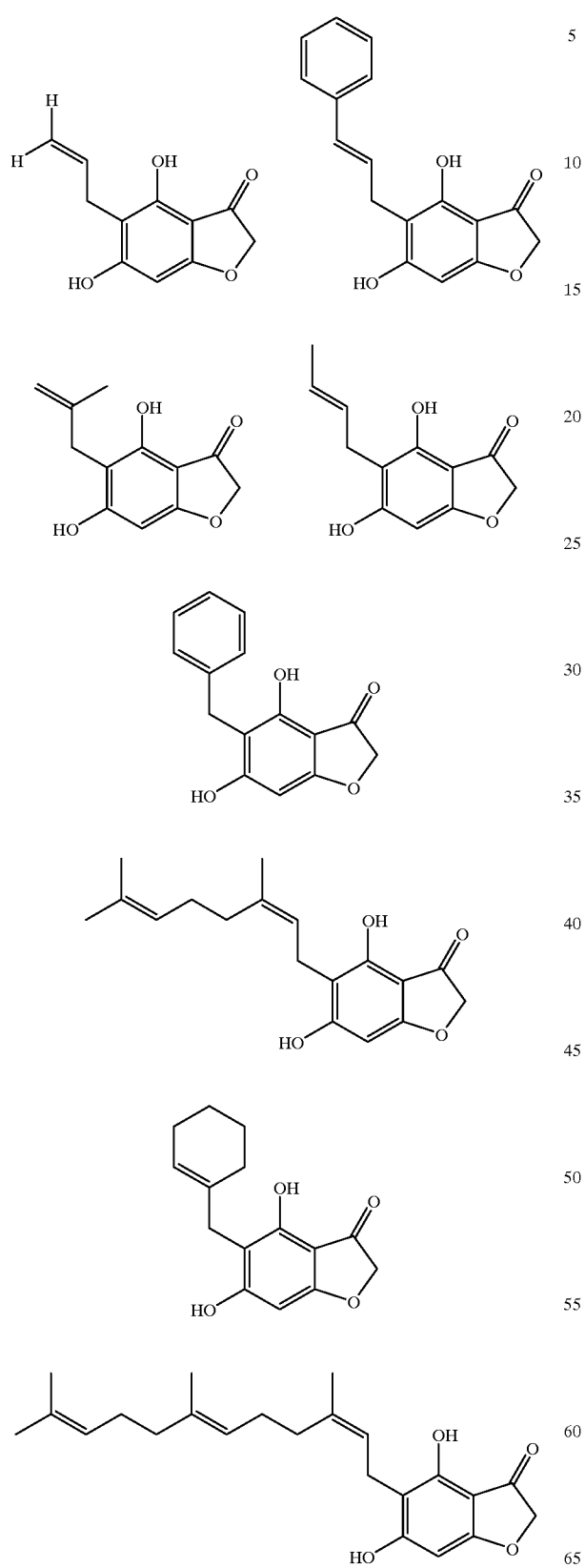
Scheme Q-2
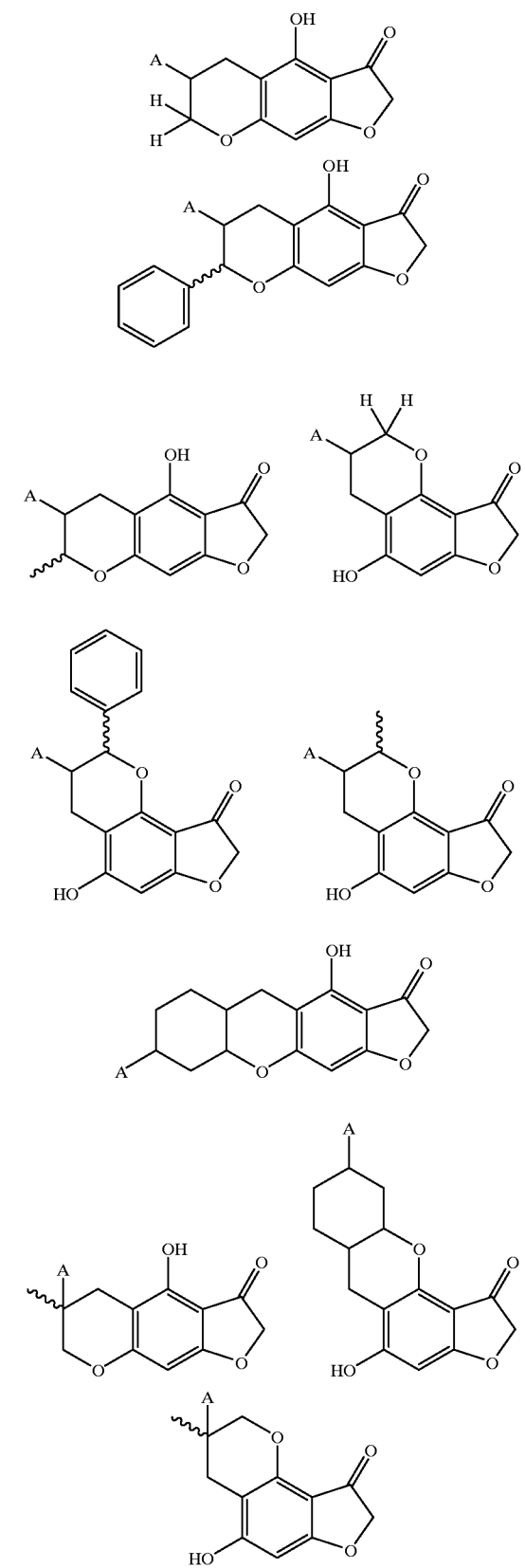

Scheme Q-3
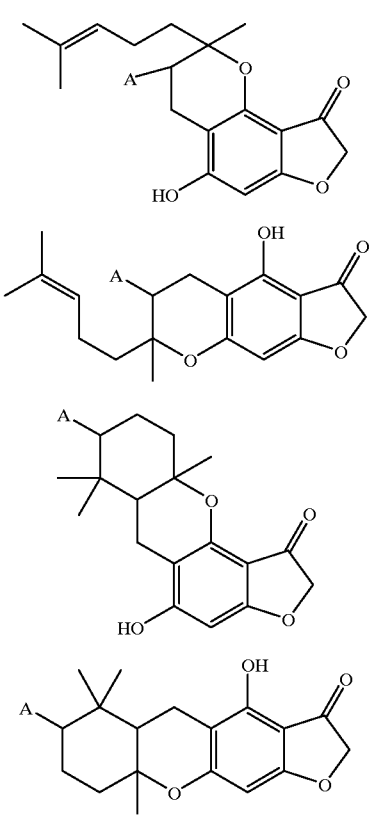
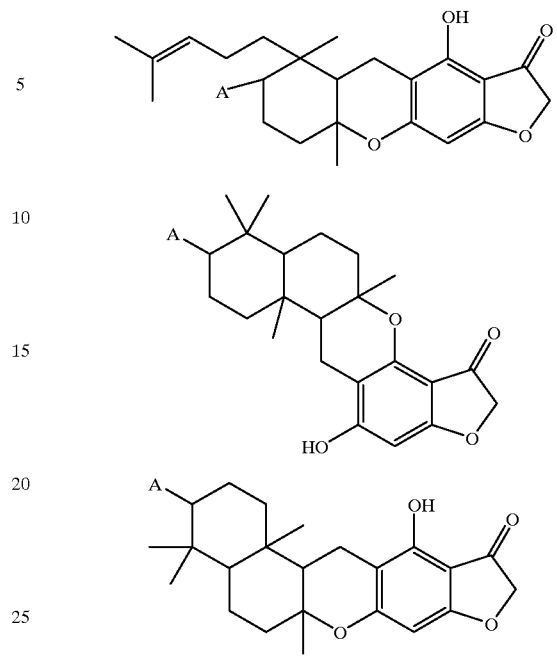
Scheme Q-4
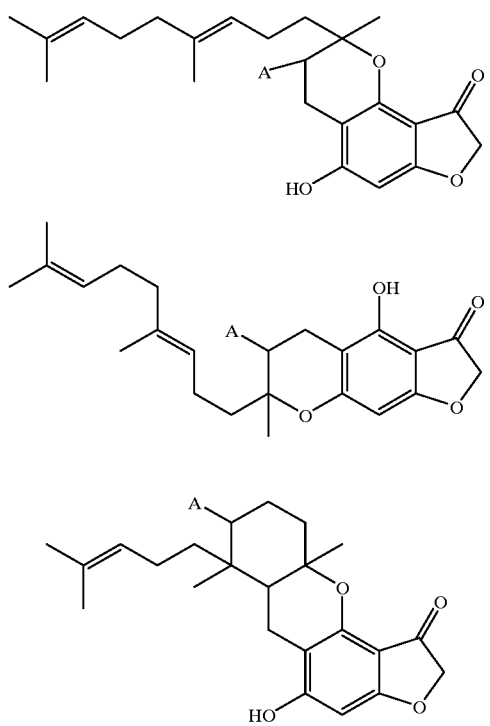
Scheme Q-5
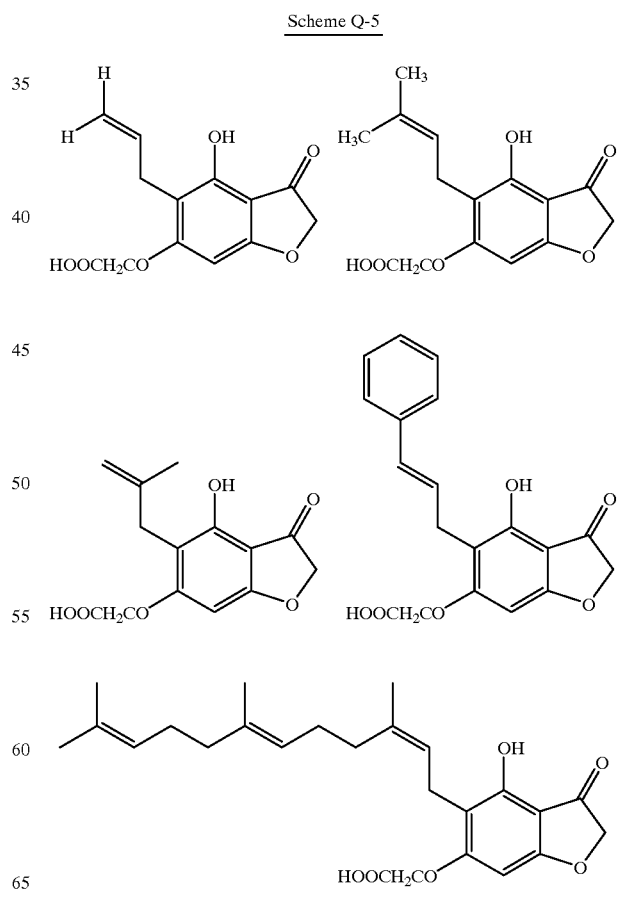

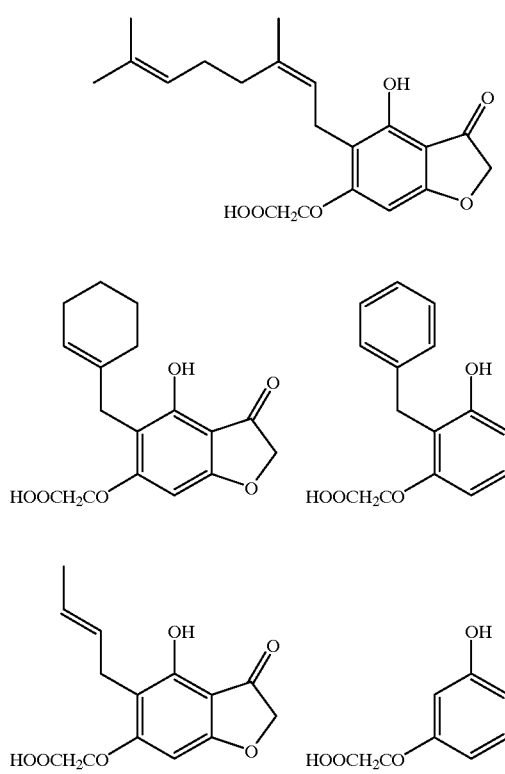
Scheme Q-6
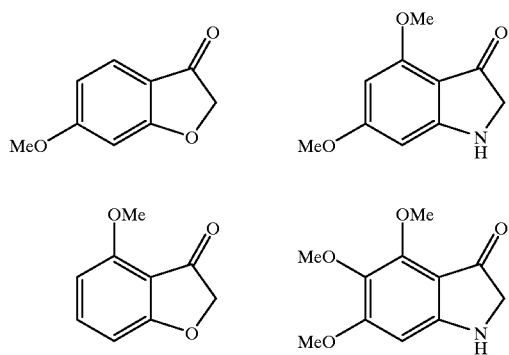
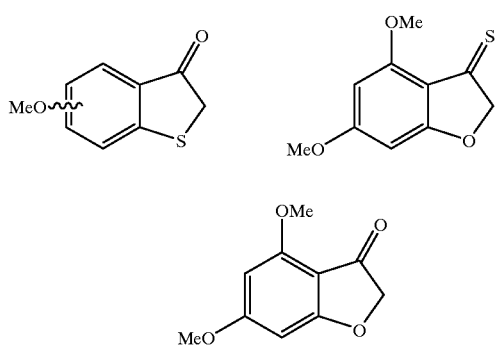
Scheme Q-7
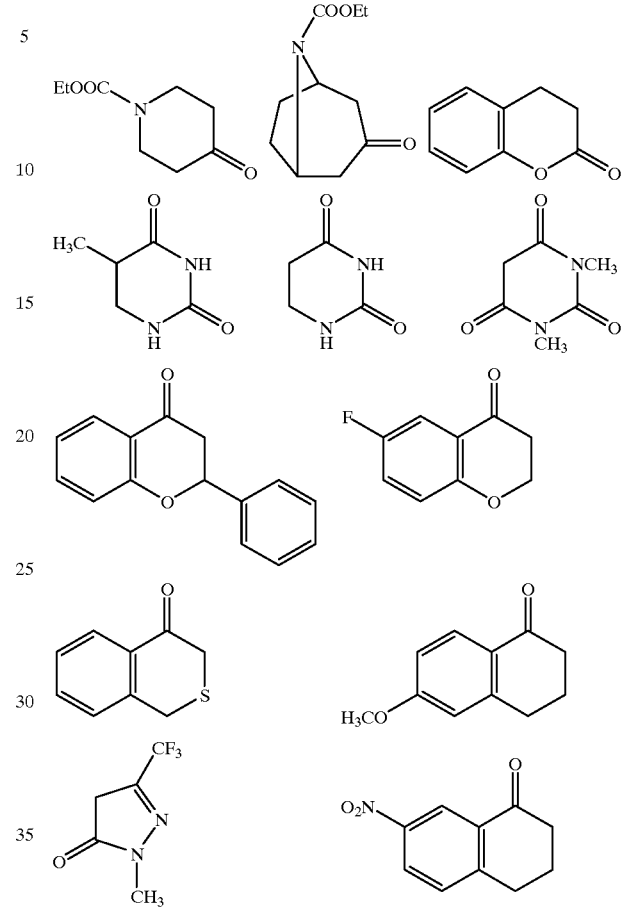
Scheme Q-8
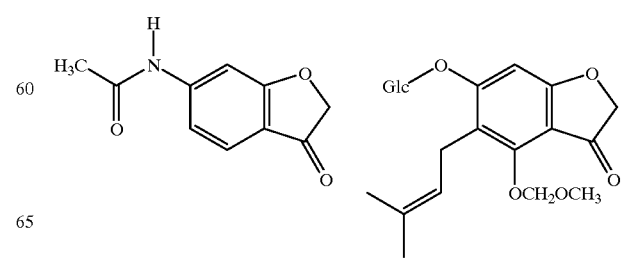

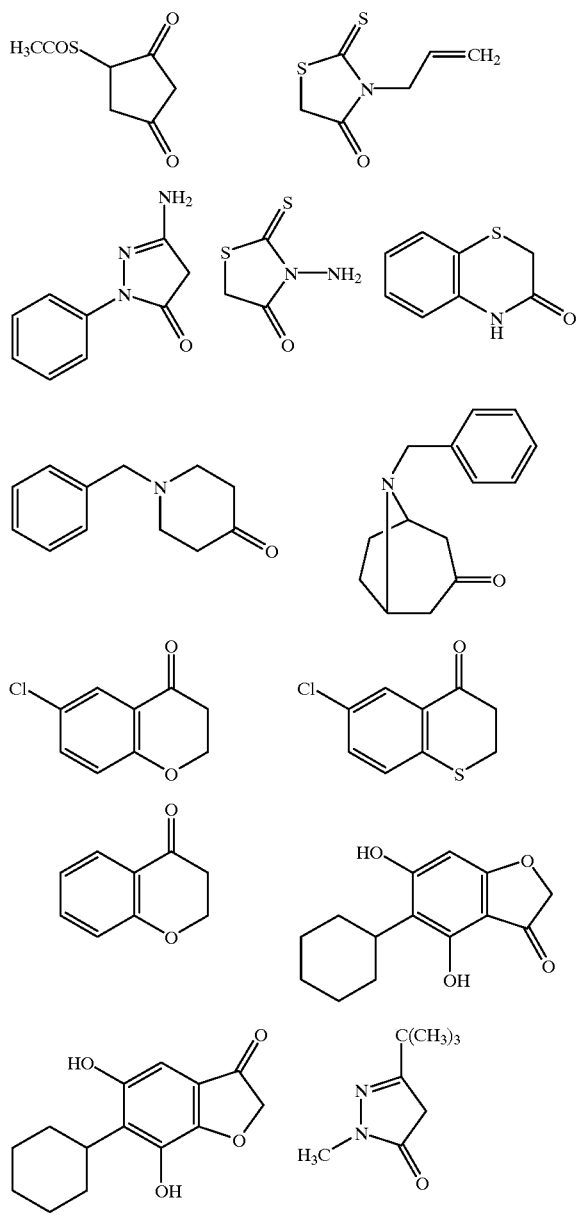
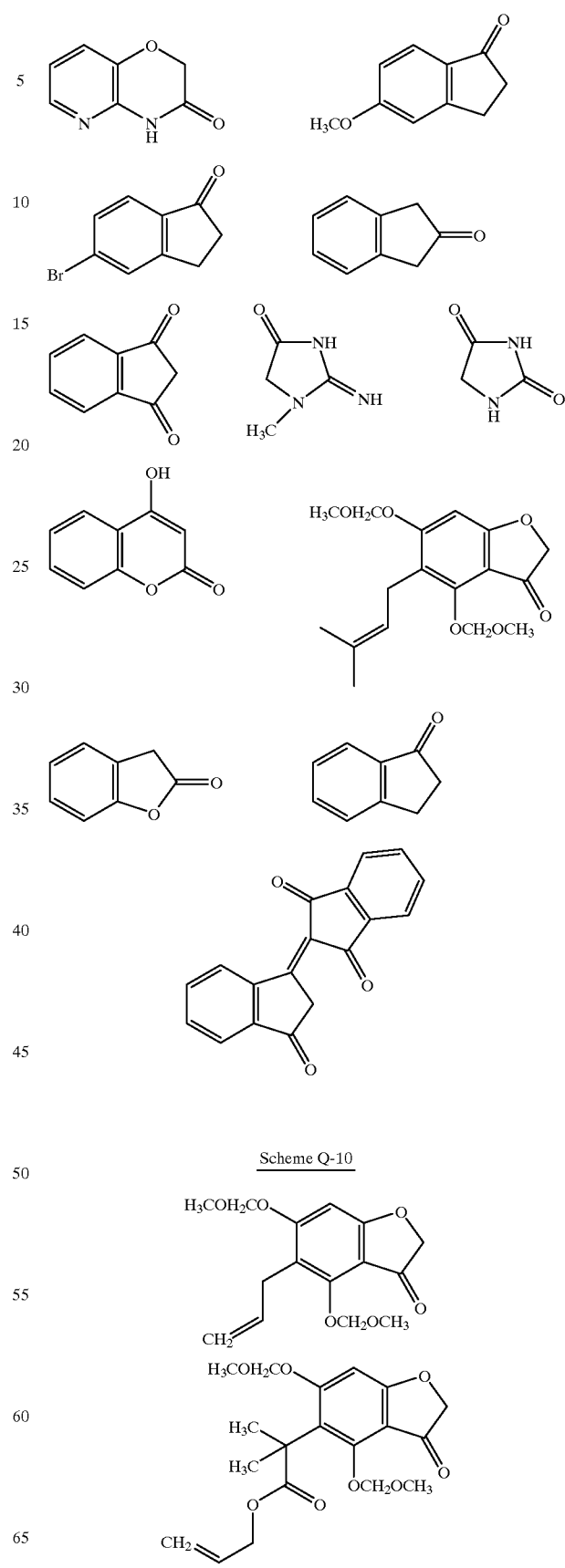
Scheme Q-9
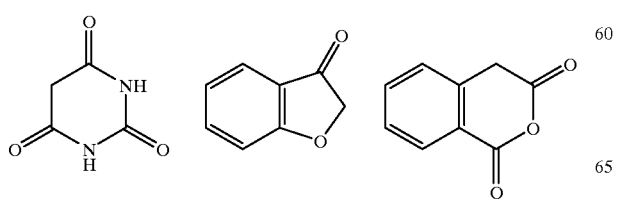

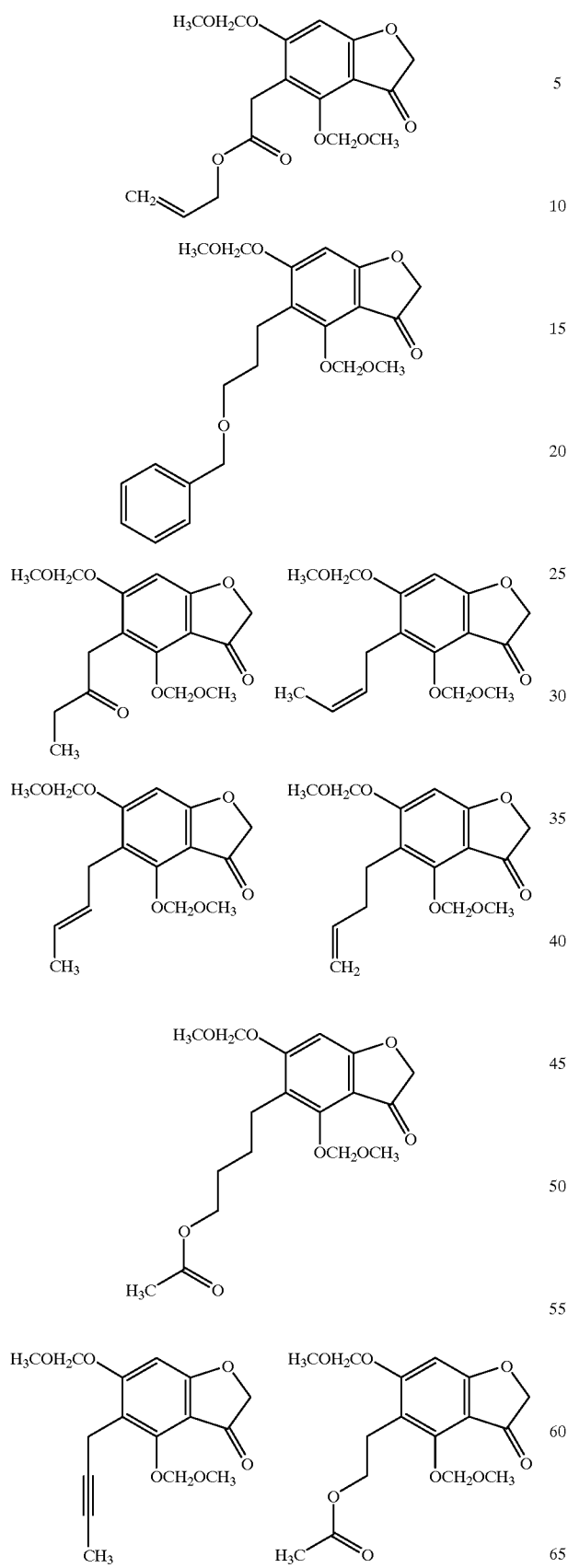
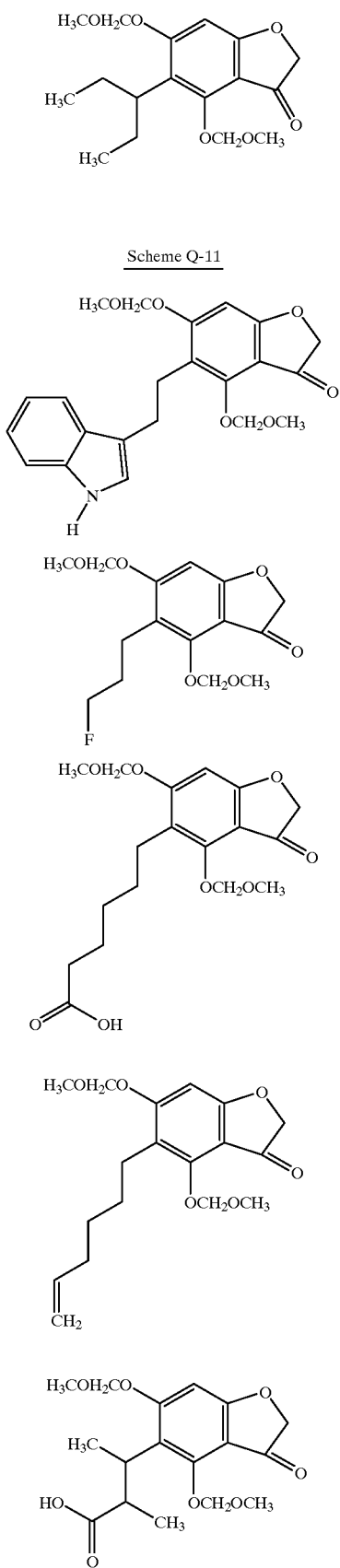
Scheme Q-11

-continued
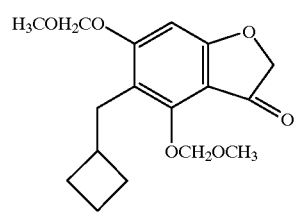
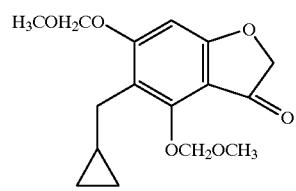
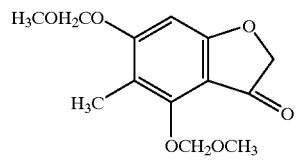
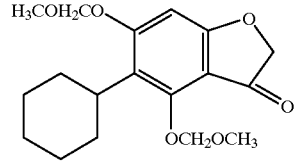
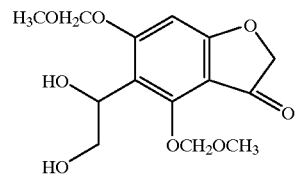
PSS057
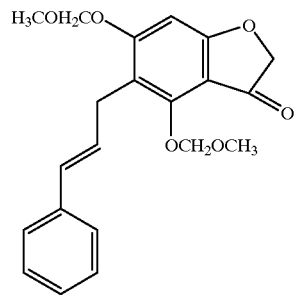
Scheme X-1
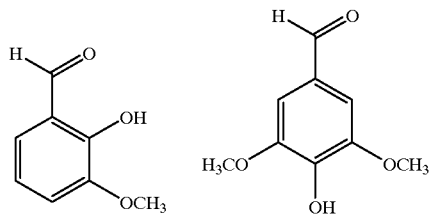
-continued
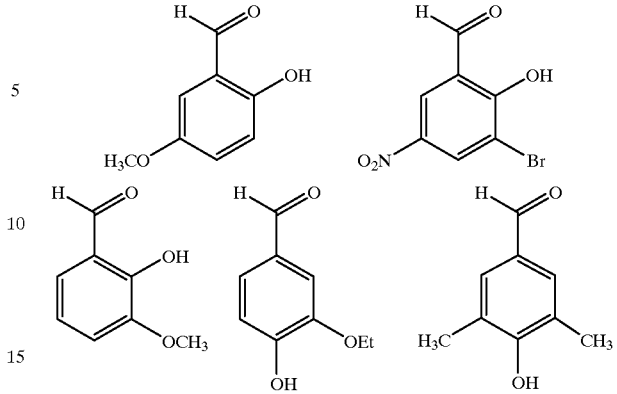
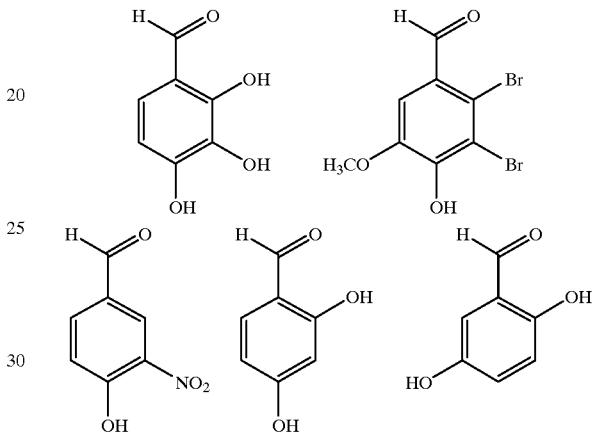
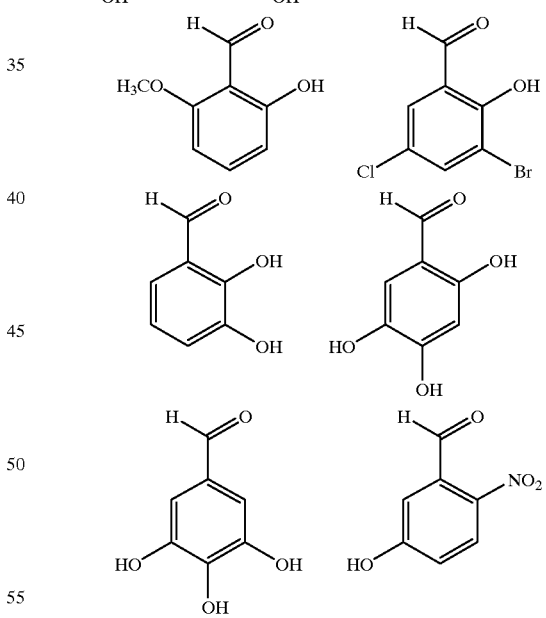
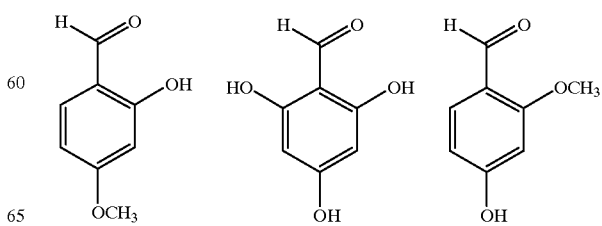

Scheme X-2
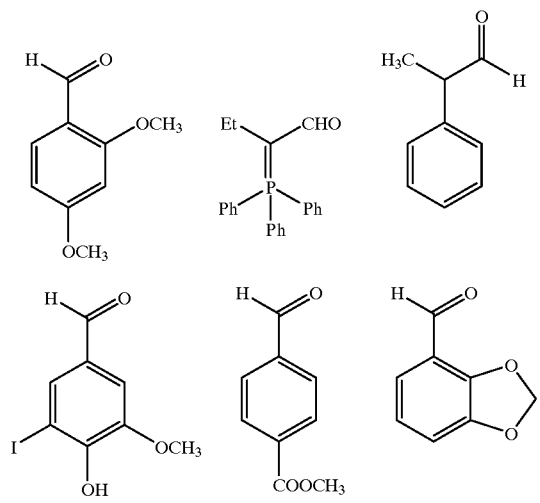
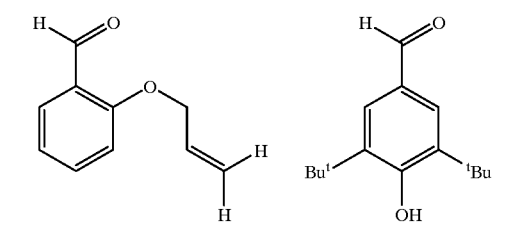
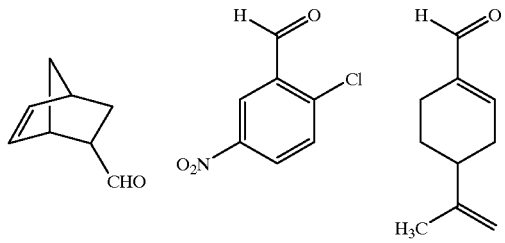
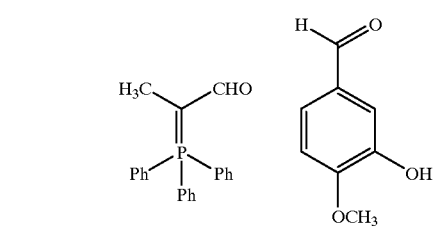
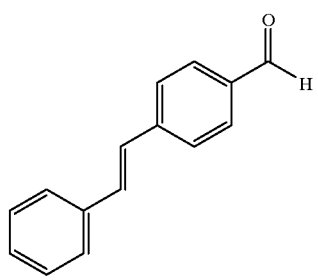
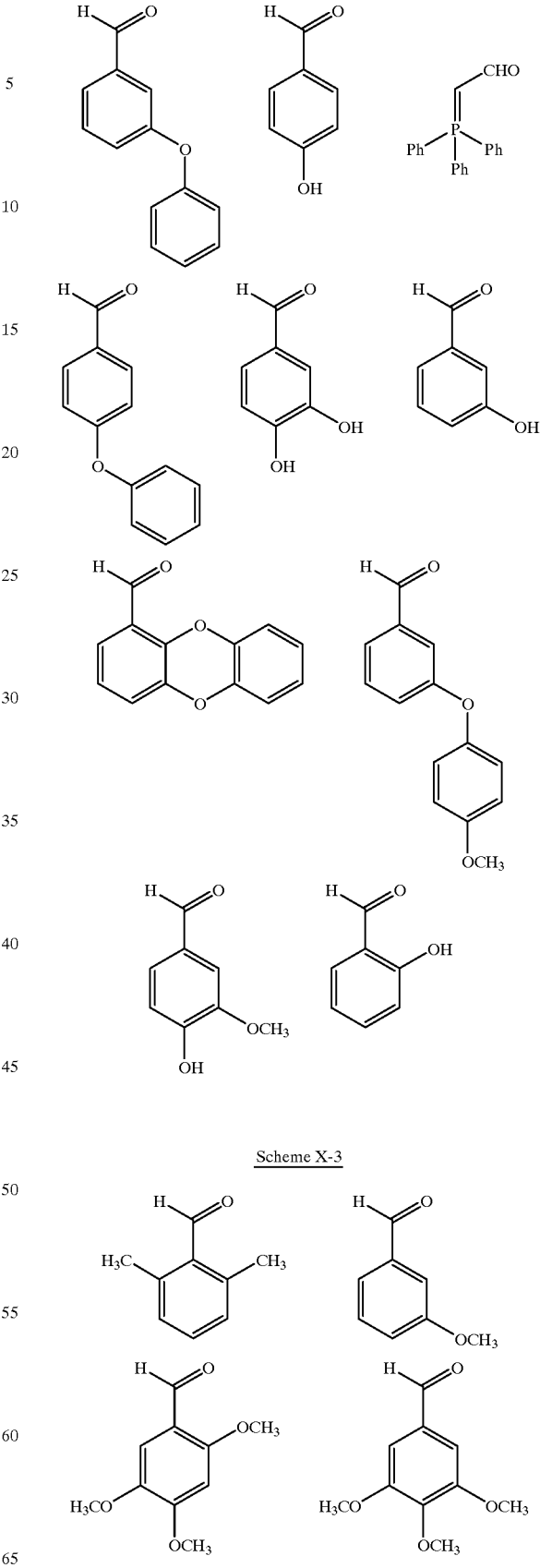
Scheme X-3

-continued
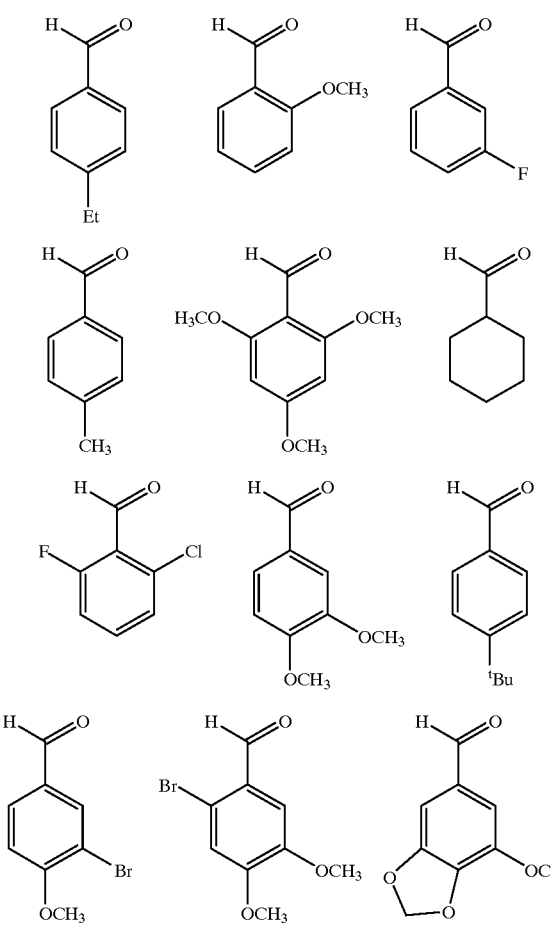
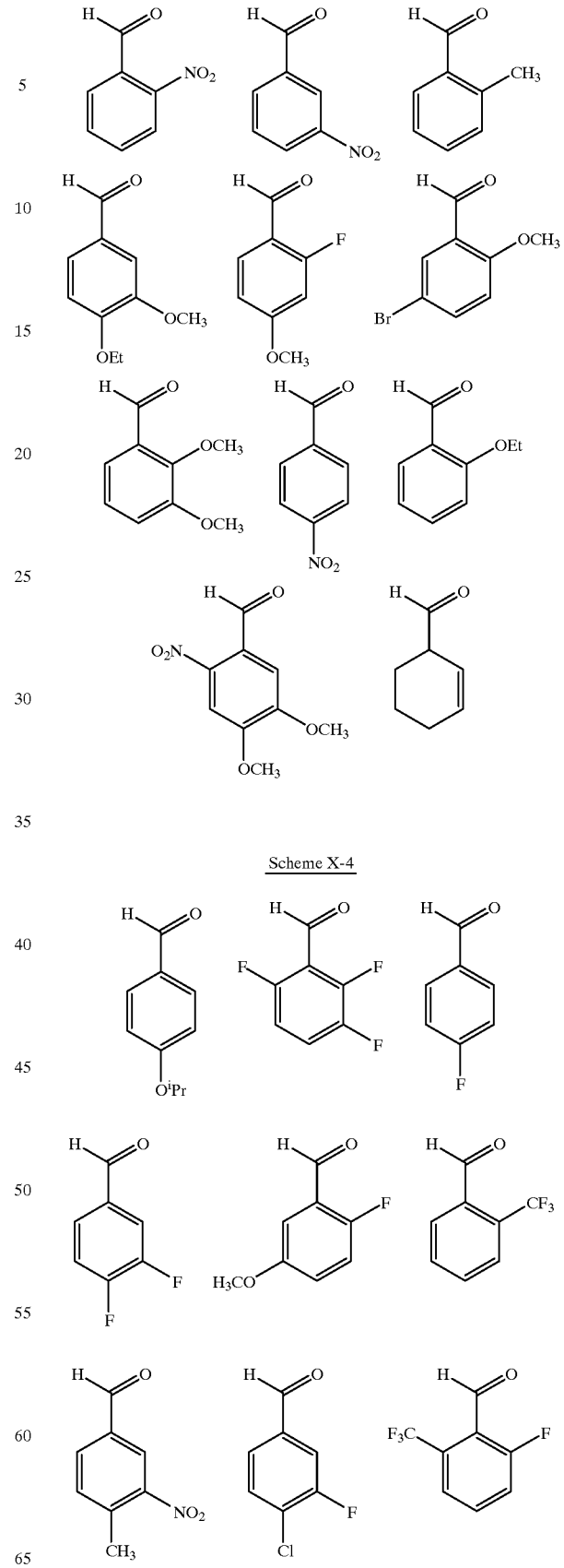
Scheme X-4

Scheme X-5
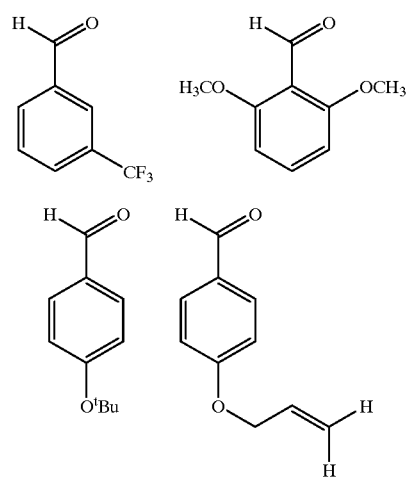
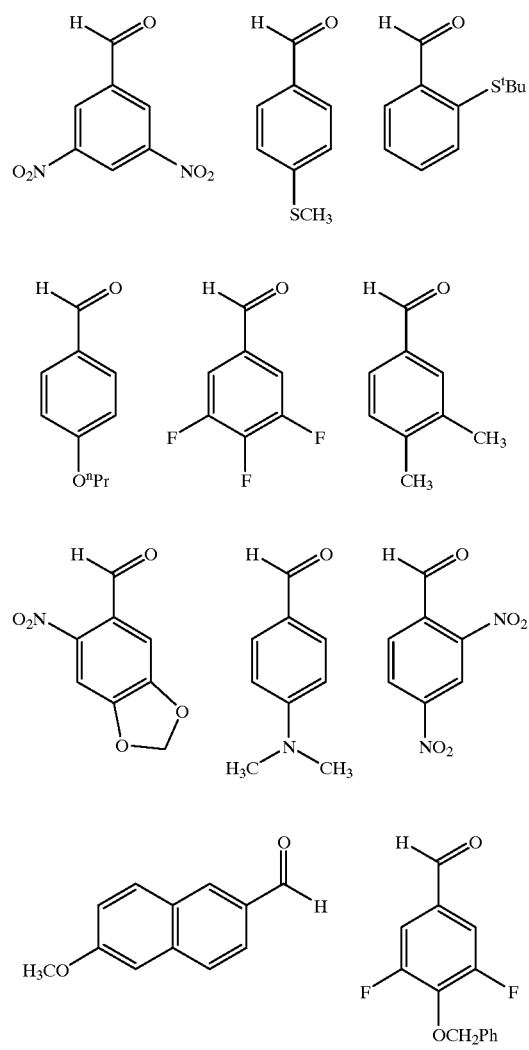
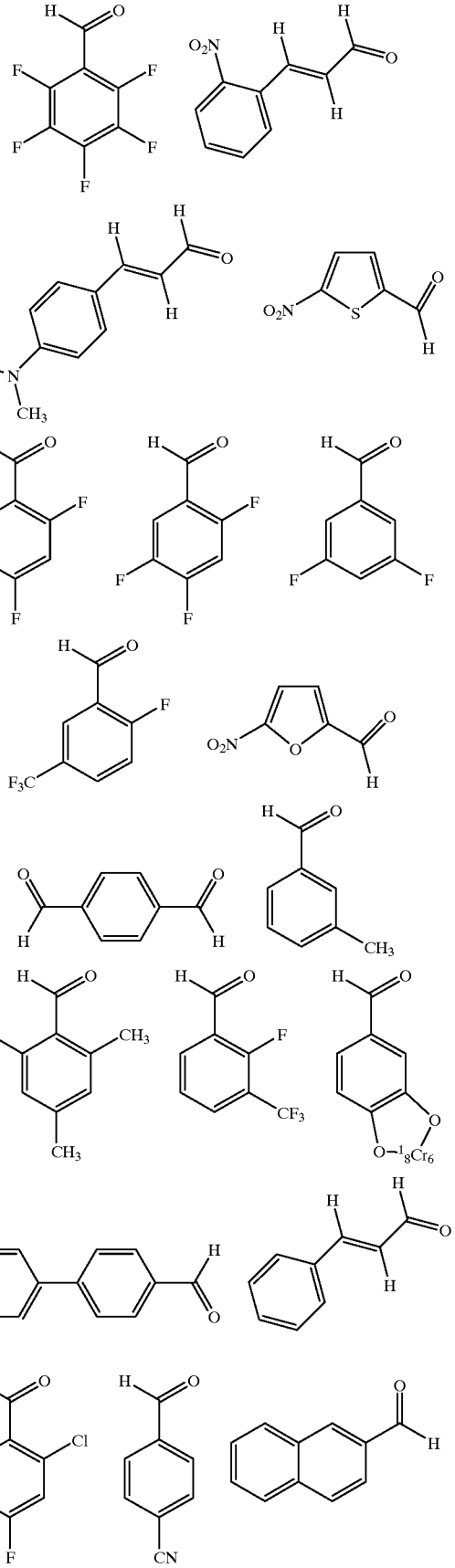

-continued
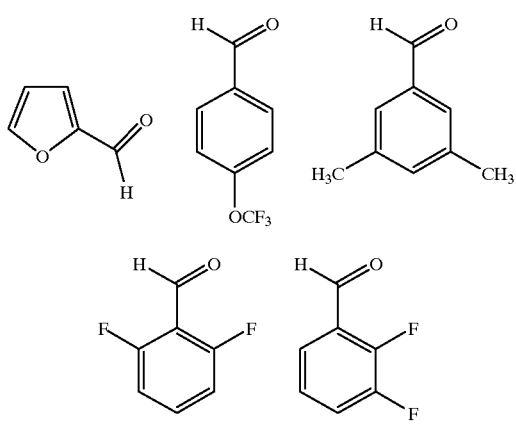
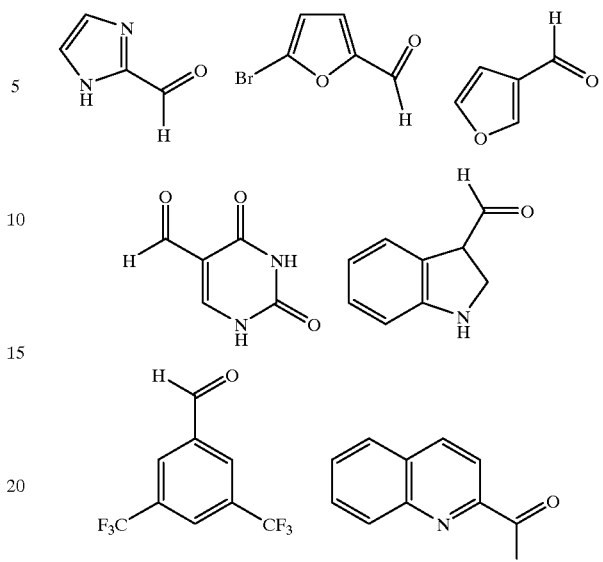
Scheme X-6
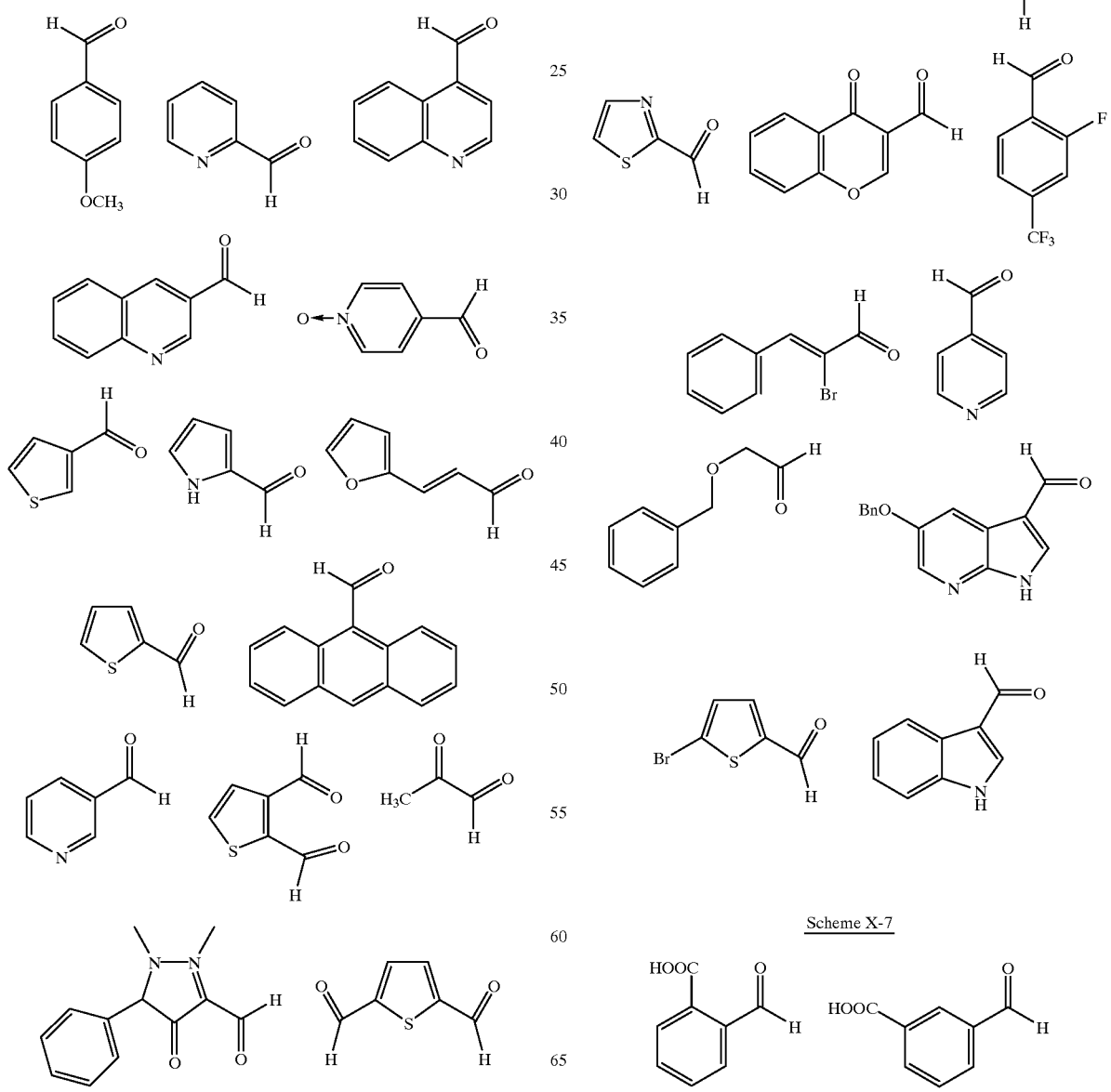
Scheme X-7

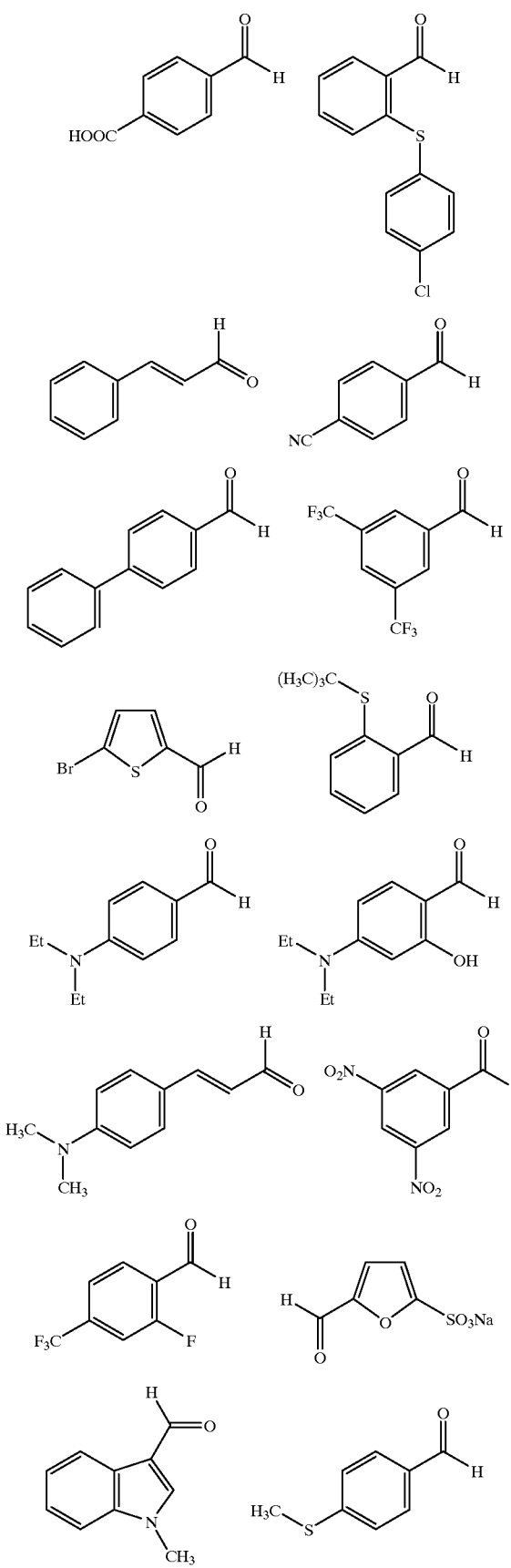
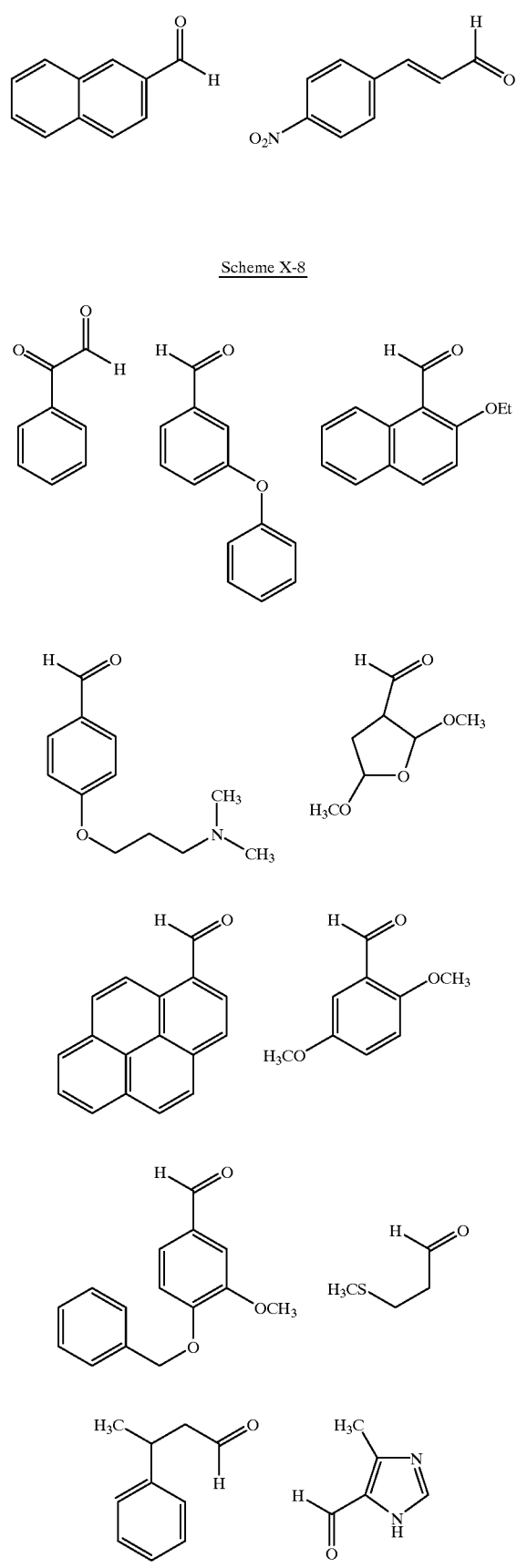
Scheme X-8

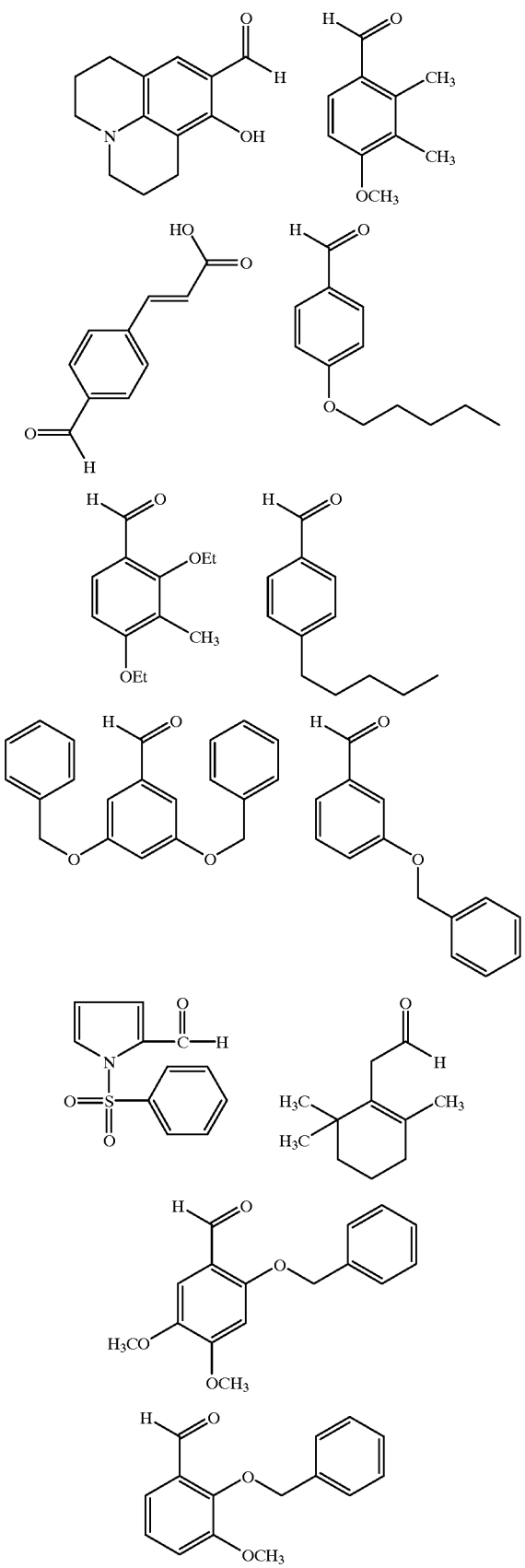
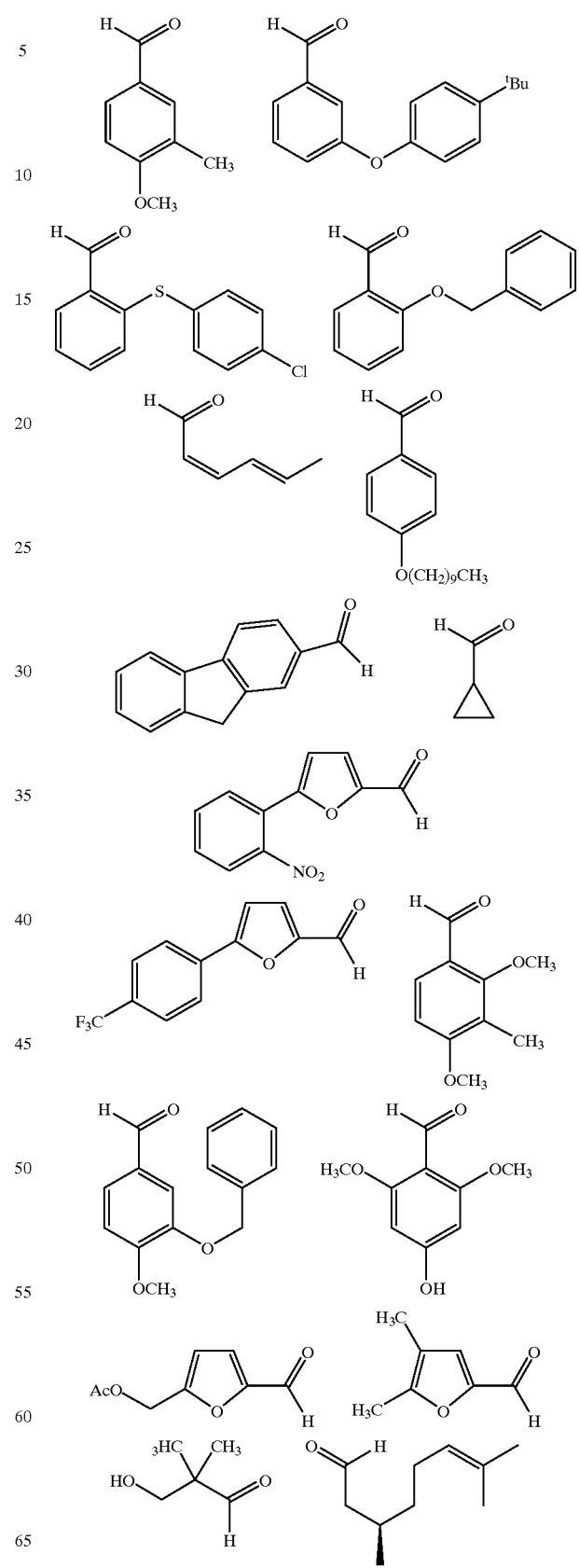
Scheme X-9

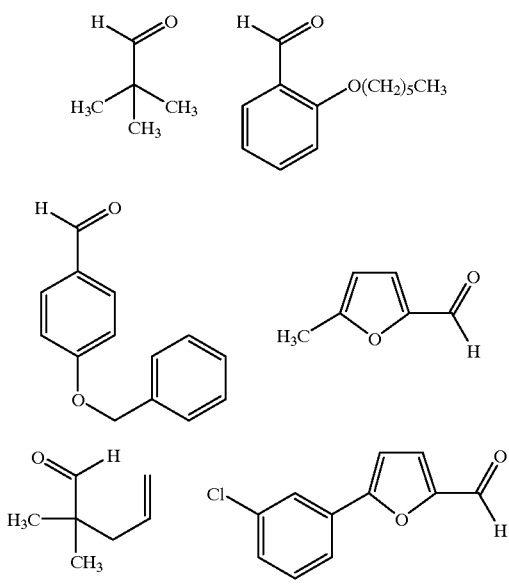
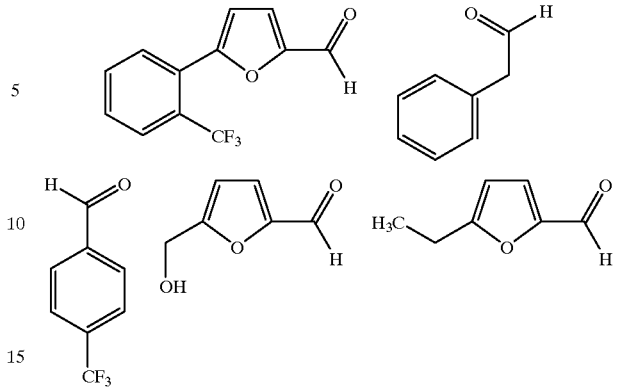

Matrix Synthesis

The compounds can also be made using matrix methodology. Over 3000 aurones were synthesized by matrix synthesis and were screened for antimicrobial activity. Numerous benzofuranones (Schemes Q-11 through Q-11) and aldehydes (Schemes X-1 through X-10) were obtained commercially or synthesized. One-hundred and sixty aldehydes were purchased.

The aldehydes were divided into two sets or plates of 80 aldehydes. Each set was reacted with a given benzofliranone. Phenolic hydroxyl groups were protected, for example, as methoxymethyl ethers. In general, the alicyclic or aliphatic aldehydes were less reactive than the aromatic aldehydes and thus required more vigorous conditions, such as higher temperatures. Even so, yields were generally lower than for the aromatic aldehydes. Portions of the adducts were screened for antimicrobial activity, and the remainder deprotected with trimethylsilyl chloride in methanol to yield the unprotected aurone, which was also screened for antimicrobial activity.

Specifically, a solution of benzofuranone in methanol, (1 M, 10 μl) was added to a 2 ml polypropylene tube containing 100 μl of methanol. After a solution of methanolic sodium methoxide (0.5 M, 22 μl) was added, the reaction was shaken for 1 minute. A solution of the aldehyde in methanol (1 M, 10 μl) was added and the reaction was left shaking for 5 minutes. After partitioning between ethyl acetate (1 ml) and water (0.5 ml), the organic layer was collected and transferred to another 2 ml polypropylene tube and allowed to dry. The dried sample was redissolved in 1 ml methanol and divided into 2 equal portions, one of which was dried and tested for antimicrobial activity. To the second portion was added trimethylsilyl chloride (50 μl). After standing at room temperature for 8 hours, ethyl acetate (1 ml) and saturated sodium bicarbonate (500 cl) were added. The organic layer was collected and dried. The dried sample was tested for antimicrobial activity.

Activity

The ability of an agent to inhibit the course of infection by a pathogenic organism ("inhibition of infection") can be directly demonstrated by an in vitro experiment measuring growth of that fungal, bacterial, or viral organism, or by using an enzyme- or cell-based inhibition assay as an indirect marker of growth. Inhibition is described by an $IC_{50}$ (concentration of test compound required for 50% inhibition) or as a MIC (the minimal inhibitory concentration, i.e., the lowest concentration of the test compound which inhibits the growth of the organism). Thus, a lower $IC_{50}$ or MIC implies improved ability to inhibit growth. A compound with increased specificity demonstrates one or more of the following: preferential inhibition of a microbial (e.g., viral, bacterial, or fungal) enzyme over a corresponding or similar enzyme in the host cell or tissue; preferential inhibition of one microbial enzyme over another microbial enzyme; and preferential inhibition of the growth of a microbe over the growth of the host cell or tissue. In general, an active compound preferably inhibits growth, measured by a given parameter, by at least 25% (e.g., at least 30%, at least 40%, at least 50%, or at least 65%) when compared to a control.

Specific examples of pharmacological assays include those which measure inhibition of the following: *Candida albicans* (e.g., ATCC #90028) growth (Example 21), fungal-specific chitin synthase (Example 22) or glucan synthase (Example 23). Additional assays measure the efficacy of the agent in prolonging the life of mice infected with a lethal challenge of either fluconazole-sensitive or fluconazole-resistant *Candida albicans* (Example 24).

A disclosed compound is therefore broadly effective against one or more Candida spp., such as *Candida albicans, C. krusei, C. glabrata, C. tropicalis, C. parapsilosis, C. guilliermorulii, C. haemulonii, C. lusitaniae, C. norvegensis, C. viswanathii,* and *C. kefyr* and others discussed in the Background section. A disclosed compound is also effective against fungal infections such as *Aspergillus fumigatus, A. flavus, A. niger, Histoplasma capsulatum* (var. capsulatum), *Coccidioides immitis, Cryptococcus neoformans* (var. neoformans, and var. gattii), *C. bidus, C. laurentii,* and *C. fusarium.* Mucormycotic organisms include *Rhizopus oryzae, R. micropsorus, R. pusillus, Cunninghamelle bertholletiae, Saksenaea vasiformis, Mucro circinelloides, M ramosissimus, Absidia corymbifera, Apophysomyces elegans, Cokeromyces recurvatus,* and *Syncephalastrum racemosum.* Certain disclosed compounds demonstrate activity against more than one type of organism and are therefore particularly suitable and effective for administration to patients with more than one type of infection (e.g., a patient may have two types of fungal infections; a bacterial infection and a viral infection; or two fungal infections and one viral infection, and so on). Certain disclosed compounds also demonstrate additivity or synergy when administered in combination with other therapeutics such as azoles (e.g., fluconazole) and amphotericin B (Example 25). Certain disclosed compounds have also been screened for mammalian cell toxicity in Vero (monkey kidney) and U937 (human monocytic) cell lines.

Antifungal Activity

Thirty-eight 96-well plates were prepared with the above samples and tested against both *C. albicans* and *A. fumigatus* at either 8 µg/ml or 12.5 µg/ml. Plates with high activity were retested at the same concentration to confirm activity.

Based on the above, preferred compounds have at least one phenolic hydroxyl group on the benzofuranone portion of the aurone, preferably at position 4 (W' in formulae II and III). Compounds with 2,3-dihydroxyphenyl or 2,3,4-trihydroxyphenyl (derived from the aldehyde reagent) exhibited good inhibition against Candida, yet exhibited little inhibition of Aspergillus. Some preferred anti-Candida compounds have polar substituents on the aldehyde portion of the aurone. Turning to anti-Aspergillus compounds, aurones including 3,5-di-t-butyl-4-hydroxyphenyl and 2,4-difluorophenyl (again derived from the aldehyde reagent) generally exhibited good inhibition. Less polar substituents tend to improve inhibition of Aspergillus.

Inhibition can be measured in terms of an $IC_{50}$, an MIC, or a percent inhibition relative to control (absence of test compound) at a given concentration, such as 8 µg/ml or 12.5 µg/ml. In general, a percent inhibition of at least 30% at 8 µg/ml or 12.5 µg/ml is preferred (e.g., at least 40%, at least 50%, at least 65%, and least 70%, and at least 85%). Preferred compounds of formula (II) exhibit a percent inhibition of at least 70%, including two as high as 87%. These compounds have formulae where W' is OH, V is 3',4'-(1,1-dimethylpropyloxy) to form a dihydropyran series, and X is selected from 3,4-dimethoxyphenyl, 4-t-butylphenyl, 2(prop-2-enyloxy)phenyl, 3-phenoxyphenyl, 3-ethoxy-4-hydroxyphenyl, 6-cyclohexenyl, and norborn-4-yl.

The inhibition values of 60 compounds are shown in Tables 1 through 3 on the next three pages.

TABLE 1

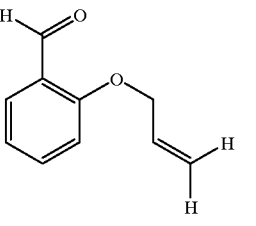
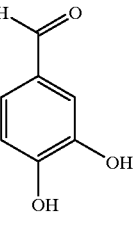
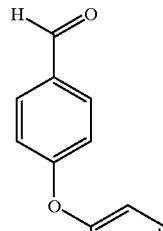

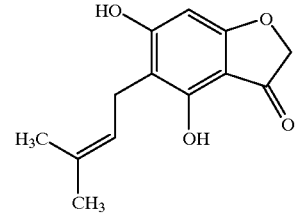

| | CA 49% | CA 92% | CA 0% |
| | AF 40% | AF 0% | AF 0% |
| | @ 12.5 µg/ml | @ 12.5 µg/ml | @ 12.5 µg/ml |

TABLE 1-continued
| | | | |
|---|---|---|---|
|  | CA 0%<br>AF 43%<br>@ 12.5 μg/ml | CA 95%<br>AF 36%<br>@ 12.5 μg/ml | CA 57%<br>AF 48%<br>@ 12.5 μg/ml |
|  | CA 67%<br>AF 94%<br>@ 8 μg/ml | CA 87%<br>AF 0%<br>@ 8 μg/ml | CA 80%<br>AF 76%<br>@ 8 μg/ml |
|  | CA 53%<br>AF 96%<br>@ 8 μg/ml | CA 0%<br>AF 0%<br>@ 8 μg/ml | CA 52%<br>AF 68%<br>@ 8 μg/ml |
| | | 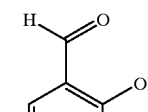 | 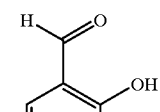 |
|  | | CA 94%<br>AF 31%<br>@ 12.5 μg/ml | CA 89%<br>AF 0%<br>@ 12.5 μg/ml |
|  | | CA 79%<br>AF 27%<br>@ 12.5 μg/ml | CA 94%<br>AF 44%<br>@ 12.5 μg/ml |
|  | | CA 96%<br>AF 52%<br>@ 8 μg/ml | CA 0%<br>AF 69%@ 8 μg/ml |

TABLE 1-continued
| | | |
|---|---|---|
| 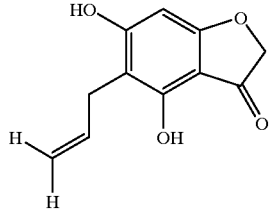 | CA 45%<br>AF 0%<br>@ 8 μg/ml | CA 69%<br>AF 35%<br>@ 8 μg/ml |
TABLE 2
| | 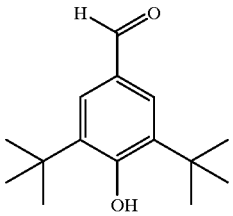 | 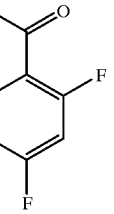 | 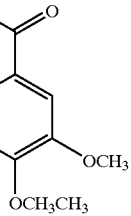 |
|---|---|---|---|
| 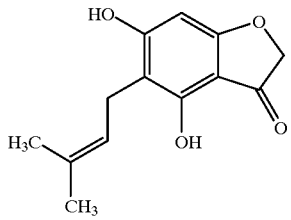 | CA 47%<br>AF 48%<br>@ 12.5 μg/ml | CA 0%<br>AF 40%<br>@ 12.5 μg/ml | CA 25%<br>AF 49%<br>@ 12.5 μg/ml |
| 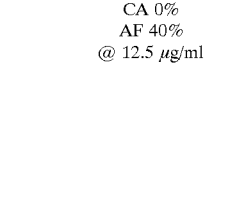 | CA 17%<br>AF 35%<br>@ 12.5 μg/ml | CA 0%<br>AF 43%<br>@ 12.5 μg/ml | CA 0%<br>AF 0%<br>@ 12.5 μg/ml |
| 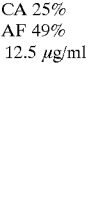 | CA 69%<br>AF 68%<br>@ 8 μg/ml | CA 0%<br>AF 94%<br>@ 8 μg/ml | CA 58%<br>AF 67%<br>@ 8 μg/ml |
| 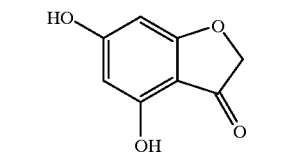 | CA 49%<br>AF 60%<br>@ 8 μg/ml | CA 53%<br>AF 96%<br>@ 8 μg/ml | CA 65%<br>AF 69%<br>@ 8 μg/ml |

TABLE 2-continued

| | 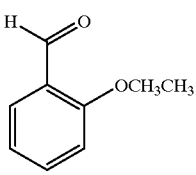 2-ethoxybenzaldehyde | 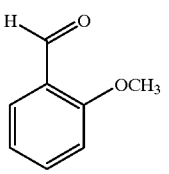 2-methoxybenzaldehyde |
|---|---|---|
| 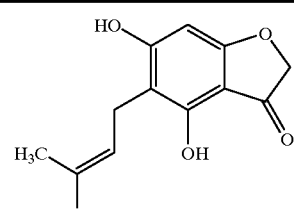 | CA 25%<br>AF 51%<br>@ 12.5 µg/ml | CA 15%<br>AF 39%<br>@ 12.5 µg/ml |
| 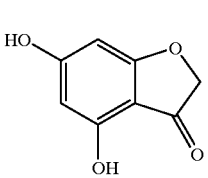 | CA 0%<br>AF 0%<br>@ 12.5 µg/ml | CA 0%<br>AF 0%<br>@ 12.5 µg/ml |
| 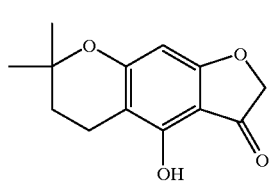 | CA 80%<br>AF 71%<br>@ 8 µg/ml | CA 76%<br>AF 70%<br>@ 8 µg/ml |
| 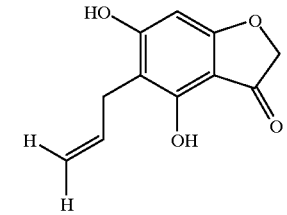 | CA 22%<br>AF 52%<br>@ 8 µg/ml | CA 20%<br>AF 62%<br>@ 8 µg/ml |

TABLE 3

| | 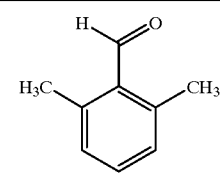 2,6-dimethylbenzaldehyde | 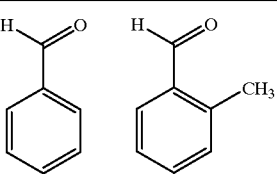 4-tert-butylbenzaldehyde | 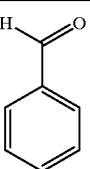 2-methylbenzaldehyde | 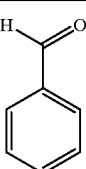 4-methylbenzaldehyde | 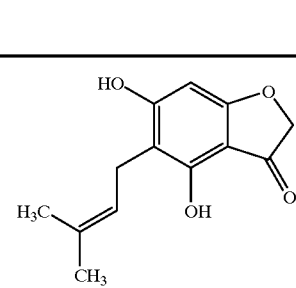 4-ethylbenzaldehyde |
|---|---|---|---|---|---|
|  | CA 7%<br>AF 0%<br>@ 12.5 µg/ml | CA 0%<br>AF 13%<br>@ 12.5 µg/ml | CA 11%<br>AF 0%<br>@ 12.5 µg/ml | CA 18%<br>AF 18%<br>@ 12.5 µg/ml | CA 31%<br>AF 41%<br>@ 12.5 µg/ml |

TABLE 3-continued

| Structure | | | | | |
|---|---|---|---|---|---|
| 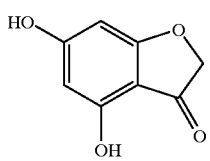 | CA 0%<br>AF 0%<br>@ 12.5 μg/ml | CA 0%<br>AF 13%<br>@ 12.5 μg/ml | CA 0%<br>AF 0%<br>@ 12.5 μg/ml | CA 0%<br>AF 0%@ 12.5 μg/ml | CA 0%<br>AF 0%<br>@ 12.5 μg/ml |
| 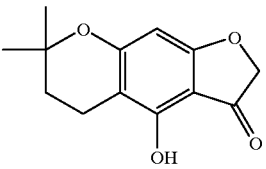 | CA 82%<br>AF 97%<br>@ 8 μg/ml | CA 87%<br>AF 94%<br>@ 8 μg/ml | CA 13%<br>AF 34%<br>@ 8 μg/ml | CA 58%<br>AF 93%<br>@ 8 μg/ml | CA 73%<br>AF 68%<br>@ 8 μg/ml |
| 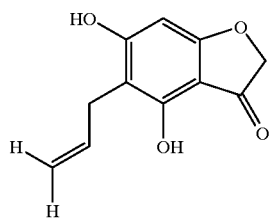 | CA 7%<br>AF 49%<br>@ 8 μg/ml | CA 56%<br>AF 69%<br>@ 8 μg/ml | CA 4%<br>AF 11%<br>@ 8 μg/ml | CA 10%<br>AF 47%<br>@ 8 μg/ml | CA 16%<br>AF 47%<br>@ 8 μg/ml |

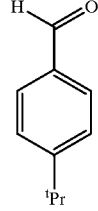

| Structure | | | |
|---|---|---|---|
| 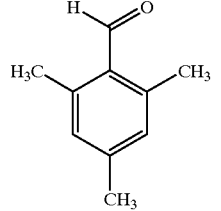 | CA 0%<br>AF 0%<br>@ 12.5 μg/ml | CA 51%<br>AF 53%<br>@ 12.5 μg/ml | CA 26%<br>AF 13%<br>@ 12.5 μg/ml |
| 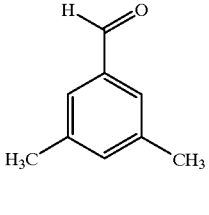 | CA 0%<br>AF 0%<br>@ 12.5 μg/ml | CA 6%<br>AF 48%<br>@ 12.5 μg/ml | CA 4%<br>AF 17%<br>@ 12.5 μg/ml |
| 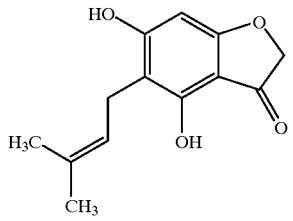 | CA 76%<br>AF 68%<br>@ 8 μg/ml | CA 0%<br>AF 28%<br>@ 8 μg/ml | CA 0%<br>AF 11%<br>@ 8 μg/ml |

TABLE 3-continued

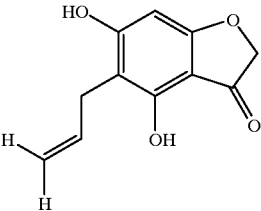

| | | |
|---|---|---|
| CA 6% | CA 16% | CA 42% |
| AF 22% | AF 7% | AF 81% |
| @ 8 µg/ml | @ 8 µg/ml | @ 8 µg/ml |

Antibacterial Activity

Compounds described herein also have activity against bacteria. The compounds shown in the table below were tested using assays known in the art and were found to have activity against *Staphylococcus aureus*.

ACTIVITY OF SELECTED AURONES AGAINST

*Staphylococcus aureus* KLE820

| STRUCTURE | % Inhibition of growth at 10 ug/ml |
|---|---|
| 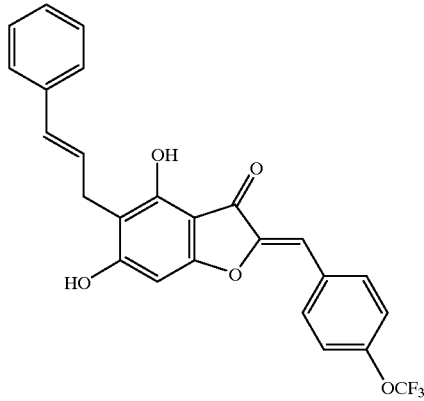 | 83 |
| 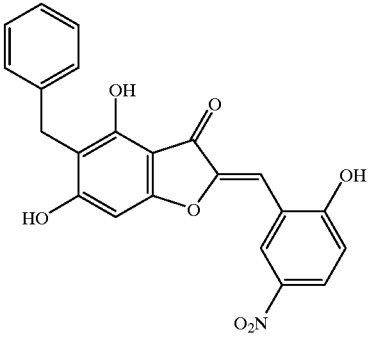 | 100 |

-continued

ACTIVITY OF SELECTED AURONES AGAINST
Staphylococcus aureus KLE820

| STRUCTURE | % Inhibition of growth at 10 ug/ml |
|---|---|
| [structure: 5-benzyl-4,6-dihydroxy aurone with 2,4,6-tribromo-3-hydroxybenzylidene] | 100 |
| [structure: 5-benzyl-4,6-dihydroxy aurone with 3,5-dichloro-2-hydroxybenzylidene] | 100 |
| [structure: 4,6-dihydroxy aurone with 4-pentyloxybenzylidene] | 98.6 |
| [structure: 5-allyl-4,6-dihydroxy aurone with 5-(2-trifluoromethylphenyl)furan-2-ylmethylene] | 76.5 |

Use

Compositions including one or more disclosed compounds are useful for inhibiting a microbial infection or combinations of infections. The invention features a method for inhibiting a microbial infection in a subject, which method includes administering a pharmaceutically effective amount of such a composition. One aspect is a method for inhibiting a fungal infection which is resistant or sensitive to known therapies, such as fluconazole or other azoles. Examples of fluconazole-resistant or fluconazole-sensitive strains include C. glabrata, C. kefyr, and C. tropicalis.

Formulation and Administration

A disclosed composition contains from about 0.1 to 90% by weight (such as about 0.1 to 20%, or about 0.5 to 10%)

of active compound(s). Disclosed compositions can be formulated as solids or liquids for oral administration, or as liquids or semi-solids (ointments, creams) for topical administration. The compositions can also be formulated for administration by nebulization or inhalation, or administration by intravenous, intramuscular, or intraperitoneal injection. Formulations for controlled release, including implantable or biodegradable or biocompatible matrices, are also contemplated. Controlled release includes continuous and intermittent release. Methods of formulation, including pharmaceutical carriers, are well-known to those in the art. The effective amount of active compound(s) used to practice the present invention for therapeutic or prophylactic treatment of conditions caused by or contributed to by a microbial infection varies depending upon the manner of administration, the age, body weight, and general health of the subject. Ultimately, the attending physician or veterinarian will decide the appropriate amount and dosage regimen. Such amount is referred to as an "effective" amount.

There now follow particular examples that describe the preparation of compounds of the invention, and the methods of the invention. These examples are provided for the purpose of illustrating the invention, and should not be construed as limiting.

EXAMPLE 1
2-Amino-4,6-dimethoxy-α-chloroacetophenone (5)

Boron trichloride (1M in $CH_2Cl_2$, 6.5 ml) was added to a dry $N_2$ flushed flask through a septum and cooled on ice. 3,5-Dimethoxyaniline (1.0 g, 6.5 mmol), dissolved in dry $CH_2Cl_2$, was added, followed by dropwise addition of chloroacetonitrile (0.500 ml, 7.8 mmol). The mixture was stirred under $N_2$ for 10 minutes, and $ZnCl_2$ (0.98 g, 7.2 mmol) was added. The green mixture was refluxed for 1 hour and stirred 18 hours at room temperature. Hydrochloric acid (2N, 5 ml) was added; the mixture was refluxed for 30 minutes, allowed to cool to 25° C., and an excess of NaOH (2N) was then added. After two extractions with $CH_2Cl_2$, the organic phases were dried ($MgSO_4$), filtered, and concentrated in vacuo to afford the crude product (1.013 g, 68%). Purification by column chromatography (eluent: $CH_2Cl_2$/MeOH: 99/1) gave (5) (834 mg, 56%). HPLC-MS: $M^+$ (230). $^1$H-NMR ($CDCl_3$, 250 MHz): δ 6.5 (broad s, 2 H); 5.65 (m, 2 H); 4.70 (s, 2 H); 3.79 (s, 3 H); 3.72 (s, 3 H).

EXAMPLE 2
4,6-Dimethoxy-3-indolinone (6)

2-Amino-4,6-dimethoxy-a-chloroacetophenone (670 mg, 2.9 mmol) was dissolved in dry acetone (10 ml). $K_2CO_3$ (604 mg, 4.4 mmol) and a little KI was added, and the mixture was refluxed for 4 hours, then stirred at room temperature for 2 days until the starting material had disappeared. The solvent was evaporated in vacuo and water (20 ml) was added to the compound. Extraction with $CH_2Cl_2$, drying with $MgSO_4$, filtration, and evaporation of the solvent in vacuo afforded the crude product. Purification by column chromatography (eluent: $CH_2Cl_2$/MeOH: 99/1) gave (6) (394 mg, 70%) as green crystals. $^1$H-NMR ($CDCl_3$, 250 MHz): δ 6.5 (broad s, 2 H); 5.65 (dd, 2 H); 4.39 (s, 2 H); 4.39 (s, 2 H); 3.82 (s, 3 H); 3.72 (s, 3 H).

EXAMPLE 3
2-Amino-4,5,6-trimethoxy-α-chloroacetophenone (8)

The target compound (8) was synthesized in the manner described for the synthesis of (5) using 3,4,5-trimethoxyaniline (2.5 g, 13.6 mmol), $BCl_3$ (1 M in $CH_2Cl_2$, 13.6 ml), $ZnCl_2$ (2.04 g, 15 mmol), and chloroacetonitrile (1.03 ml, 16.3 mmol) in dry $CH_2Cl_2$. Purification by column chromatography as described for (5) afforded (8) (1.06 g, 30%) as a cystalline product. $^1$H-NMR ($CDCl_3$, 250 MHz): δ 6.5–5.5 (broad s, 2 H); 5.9 (s, 1 H); 4.70 (s, 2 H); 3.95 (s, 3 H); 3.80 (s, 3 H); 3.65 (s, 3 H).

EXAMPLE 4
4,5,6-Trimethoxy-3-indolinone (9)

Compound (9) was synthesized from (8) in the same manner as described for the synthesis of (6) using 2-amino-4,5,6-trimethoxy-a-chloroacetophenone (1.05 g, 4.0 n-mmol), $K_2CO_3$ (838 mg, 6.1 mmol), a little KI, and dry acetone (50 ml). Purification by column chromatography (eluent: $CH_2Cl_2$/MeOH: 9/1) afforded (9) (190 mg, 21%) as red crystals.

EXAMPLE 5
Preparation of 6-methoxy-3-benzofuranone

Chloroacetonitrile (3.5 ml, 55.2 mmol) was added dropwise to a stirred solution containing 3-methoxyphenol (5 ml, 46 mmol) and zinc chloride (6.9 g, 50.6 mmol) in anhydrous dioxane (30 ml) at room temperature. The resulting solution was saturated with dry hydrogen chloride gas. After stirring at room temperature overnight, the yellow precipitate was filtered and washed with anhydrous ether (100 ml). The collected precipitate was dissolved in water (80 ml) and heated to reflux for 1 hour. The solution was allowed to cool to approximately 40° C., and aqueous sodium hydroxide (20% w/v) (7.5 ml) was added. After stirring at that temperature for 30 minutes a pale yellow precipitate had formed. A heterogeneous system was then taken to pH≈7 by addition of hydrochloric acid (1 M). The precipitate was filtered, washed with water, and recrystallized from acetone to give the desired compound as a light yellow powder (4.14 g, 54.8%). $^1$H NMR: 8 (ppm): 3.85 (OMe); 4.9 (CH2); 6.50–6.46 (2 H-Phenyl); 7.70–7.66 (1 H-Phenyl).

EXAMPLE 6
Preparation of 6-methoxy-3-benzothiofuranone or 4-methoxy-3-benzothiofuranone Chloroacetonitrile (0.62 ml, 9.8 mmol) was added dropwise to a stirred solution containing 3-methoxythiophenol (1 ml, 8.1 mmol) and aluminum chloride (1.19 g, 8.9 mmol) in anhydrous ether (10 ml) at room temperature. The resulting solution was saturated with dry hydrogen chloride gas. After stirring at room temperature overnight, the pale yellow precipitate was filtered and washed with anhydrous ether (30 ml). The collected precipitate was dissolved in water (25 ml) and heated to reflux for 1 hour. After cooling to approximately 40 (C, aqueous sodium hydroxide (20% w/v) (2.6 ml) was added. After stirring at that temperature for 30 minutes the solution was then adjusted to pH≈7 by the addition of hydrochloric acid (1 M). The resulting solution was extracted with ethyl acetate (2×50 ml). The combined organic extracts were washed with brine, dried over magnesium sulfate, and concentrated in vacuo to afford an orange oil. Column chromatography, using dichloromethane with 1% methanol, gave a light yellow solid (770 mg, 52.8%), a single compound by TLC and HPLC.

EXAMPLE 7
Preparation of 4,6-dimethoxy-3-benzofuranone

Benzofuranone (3 g, 18.1 mmol) was dissolved in DMF (100 ml). To this was added $Li_2CO_3$ (5.4 g, 72.4 mmol) and methyl iodide (3.5 ml, 54.3 mmol) in one portion. A nitrogen atmosphere was maintained, and the reaction was stirred for 18 hours at 70° C. The mixture was filtered, and water was added to the solution. The DMF/water phase was extracted with dichloromethane (3×100 ml) and the organic phase was washed with a saturated NaHCO$_3$ solution (2×100 ml). After drying with MgSO$_4$ and concentrating the solution, solid yellow crystals formed. These were washed with cold ethanol to give a single compound by HPLC. Yield: 2.2 g (73%).

EXAMPLE 8
Preparation of 4,6-dimethoxy-3-benzofuranthione

This reaction was performed under nitrogen and anhydrous conditions. 4,6-Dimethoxy-3-benzofuranone (1.5 g, 6.6 mmol) was dissolved in dry toluene (25 ml), and Lawesson's reagent (1.6 g, 4 mmol) was added. The mixture was refluxed with stirring for 18 hours. The mixture was cooled to room temperature and purified by chromatography with 1:1 ether:petroleum ether. Concentration of the fractions yielded yellow/orange crystals. The crystals were washed with the eluent and clean yellow crystals were produced. $^1$H NMR showed at least two compounds, probably the thioketone and the thiol. Yield: 400 mg (27%). NMR: δ (ppm): 3.86, 3.88, 3.94, 3.96 (OMe, 2 from thioketone and 2 from thiol), δ (ppm): 4.04 (—OCH$_2$C(S)—), δ (ppm): 6.40 6.52 (aromatic).

EXAMPLE 9
4-Methoxy-3-benzofuranone (2) and 6-methoxy-3-benzofuranone (3)

These compounds were prepared from 3-methoxyphenol (1) (6 ml, 55 mmol), ZnCl$_2$ (8.2 g, 60 mmol), and chloroacetonitrile (4.2 g, 66 mmol) in dry ether (100 ml). Purification of the crude product by column chromatography (eluent: CH$_2$Cl$_2$/MeOH: 99/1) gave (2) (1.147 g, 13%), a single compound by HPLC (98% pure, recrystallized from EtOH). $^1$H-NMR (Acetone-d$_6$, 400 MHz): (7.45 (1 H, d); 6.64 (2 H, m); 4.62 (s, 2 H); 3.95 (s, 3 H) and the more polar compound (3) (1.48 g, 17%). HPLC (84% purity). $^1$H-NMR (Acetone -d$_6$): δ (400 MHz): values corresponded to previous synthesis of (3).

EXAMPLE 10
4,6-Bismethoxymethoxybenzofuranone

To two grams (12 mmol) benzofuranone dissolved in 100 ml DMF was added 6 ml triethylamine. After adding 2.8 ml (36 mmol) methoxymethyl chloride (MOM-Cl) dropwise over 15 minutes, the solution was stirred for 18 hours at room temperature. Water (100 ml) was added to quench the excess MOM-Cl. The resultant mixture was extracted with 100 ml brine, dried with MgSO$_4$, and concentrated to give a brown oil which contained some DMF. Chromatographic purification (3:1 ethyl acetate:hexane with 2% diisopropylethylamine) gave the di-MOM protected benzofuranone as an oil. Recrystallization from water gave the product as fine, light brown needles (2.6 g, 70%).

EXAMPLE 11
4,6-Bismethoxvmethoxybenzofuranone thioketone

This reaction was performed under nitrogen and anhydrous conditions. To a solution of the product of Example 12 (0.3 g, 1.35 mmol) dissolved in 15 ml dry toluene was added Lawesson's reagent (0.36 g, 0.9 mmol). The reaction was refluxed overnight until the ketone was consumed, by TLC. Chromatographic purification (3:1 dichloromethane: petroleum ether and 2% diisopropylethylamine; or 3:1 ether:petroleum ether and 2% diisopropylethylamine) gave a slightly yellow clear oil. TLC showed a major and minor product.

EXAMPLE 12
Inhibition of Fungal Growth

Test compounds were tested against nine isolates in an eight-point dose response assay ranging from 50 μg/ml to 0.39 μg/ml. Aspergillus MIC's (minimum inhibitory concentrations) were scored visually after 48 and 72 hours at 37° C. All Candida MIC's were scored visually after a 24 hour incubation at 35° C. Amphotericin B (2.5 μg/ml) and 5-flucytosine (2.0 μg/ml) were standard controls for each antifungal assay. In each case, total inhibition was observed for all assays relative to amphotericin B and 5-flucytosine. The results are shown below in Table 4, MIC values in μg/ml after 72 hours. HFF toxicity was analyzed after a 24 hour incubation at 37° C. (5% CO$_2$). MTS/PMS was added, and the sample absorbance was read at 450 nm.

TABLE 4

Minimum Inhibitory Concentrations

| Pathogen | S02 | S12 | S17 |
|---|---|---|---|
| [a]A. fumigatis ATCC8001 (XI) | 12.5 | 12.5 | 6.25 |
| [a]A. fumigatus ATCC8001 (X2) | 6.25 (>50) | 6.25 (50) | 6.25 (25) |
| [b]A. fumigatus 94-2766 | 6.25 (>50) | 6.25 (50) | 6.25 (>50) |
| [c]A. niger | >50 (>50) | 50 (50) | 12.5 (50) |
| C. albicans ATCC90028 | 12.5 | 12.5 | 3.125 |
| C. tropicalis ATCC750 | 12.5 | >50 | >50 |
| C. krusei ATCC6258 | 6.25 | 6.25 | 6.25 |
| [d]C. glabrata (Fluconazole resistant) | 0.39 | 0.39 | 0.39 |
| C. parapsilosis ATCC90018 | 6.25 | 6.25 | 12.5 |

[a]Reference strain from Chrisope Technologies
[b]Clinical isolate from J. R. Graybill
[c]Clinical isolate from A. Sugar
[d]Clinical isolate from M. Rinaldi

EXAMPLE 13
Harvesting of Cells

Seeds were sterilized in a 5% sodium hypochlorite solution (4.8% active chlorine) such as DOMESTOS™ (Lever Industries Ltd, Runcom, Cheshire, UK) for 15 minutes, then washed several times in sterile distilled water. The plant cell cultures FR2920 and FR2083 were derived from seeds of species Ficus religiosa (B&T World Seeds, Fiddington, Somerset, UK; and Chiltem Seeds, Ulverston, Cumbria, UK).

The following media were used: B20, Gamborgs B5 (no hormones, 2% sucrose); B5, Gamborgs B5 (2,4-D 1 mg, kinetin 0.1 mg, 2% sucrose); and B48, Gamborgs B5 (NAA 0.1 mg, kinetin 0.5 mg, 2% sucrose). Cultures were grown in continuous low light at 25° C. Suspensions were agitated at 140 rpm.

Sterile seed was placed upon seed germination medium (B20) to germinate. After the appearance and appropriate growth of roots and/or shoots from 5–10 seedlings on agar, roots and/or shoots were dissected, chopped into small pieces approximately 5 mm long and placed in 20 mL liquid media for suspension initiation (medium B5 or B48) in a 100 mL flask.

Two 16 mL aliquots of medium were added, at 10 days and at 17 days after dissection and placement in medium. Four weeks after the second medium addition, the entire contents of the flask were transferred to a 250 mL flask containing 100 mL of fresh medium. After 3 more weeks, 40 mL of the new suspension was transferred to 100 mL of fresh medium in a 250 ml flask, and the suspension was thereafter subcultured at 2-week intervals by regular transfer of 28–40 mL of 14-day cultures to 100 mL fresh medium.

Two treatments (T4 and T3) were used. In T4, a 40 mL aliquot of the suspension at day 0 was transferred to a 100 mL flask. On day 3, a sterile solution of 5-azacytidine (5-AC) in water was added for a final concentration of $3\times10^{-5}$ M, and the resultant mixture was incubated for 11 days. At this point the 40 mL 5-AC-treated culture was subcultured two times before adding the contents of the 2×250 mL flasks to a 2 L flask containing 750 mL production medium B49 (Gamborgs B5, 5% sucrose, no hormones). After 7 days growth, additions of filter-sterilized methyl jasmonate (250 µM final concentration) and an autoclaved *Candida albicans* preparation (50 mg/L final concentration) were made. After a further 4–6 days incubation the cultures were harvested by vacuum filtration.

The T3 treatment was identical to the T4 treatment except the 5-AC treatment was omitted. Thus, after two subcultures, the contents of 2×250 mL flasks were added to a 2 L flask containing 750 mL production medium, and so on.

After harvesting, the separated cells were freeze-dried before extraction. The separated medium was frozen pending further analysis.

EXAMPLE 14

Extraction and Isolation

Freeze dried cell culture biomass (91 g) from Example 13 was extracted with water (deionized) followed by a 1:1 solvent mixture of methylene chloride and methanol. The organic solvent extract was dried (20 g) under vacuum and chromatographed on C-18 silica (400 g) using 500 mL each of following solvents: water; 20% methanol in water; 40% methanol in water; 60% methanol in water; 80% methanol in water; methanol; 25% chloroform in methanol; 50% chloroform in methanol; 75% chloroform in methanol; and chloroform respectively. Ten fractions, 500 mL each, were collected. Fraction 6, the most active fraction, was further chromatographed on SEPHADEX™ LH-20 (100 g) and eluted with methanol. Fraction volumes between 10 and 15 mL were collected.

Fractions 10–12 were combined and further purified on a MCI gel column using a mixture of methanol:water (80:20) as the mobile phase. Fraction volumes of 10–15 mL were collected. Fractions 38–50 were pooled to yield 60 mg of formula (V). EIMS yielded a m/z value of 354 (M+). Proton and carbon NMR data are given in Table I and II, respectively.

Fractions 20–25 of the SEPHADEX™ LH-20 column were combined and purified on a MCI gel column using a mixture of methanol:water (70:30) as the mobile phase. Fraction volumes of 10–15 mL were collected. Fraction 23 yielded 12 mg of formula (VI). EIMS yielded a m/z value of 638 (M+). Proton and carbon NMR data are given in Table III.

Formula (V) is shown in the Summary section; formula (VI) is shown below.

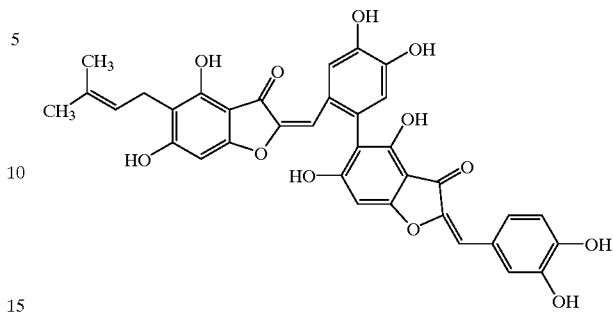

(VI)

TABLE I $^1$H NMR (300 MHz, CD$_3$OD)
Formula (V)

| | |
|---|---|
| 7 | 6.56 (1H, s) |
| 8 | 6.26 (1H, s) |
| 1" | 3.26 (2H, d, J = 7.2 Hz) |
| 2" | 5.20 (1H, t, J = 7.2 Hz) |
| 4" | 1.77 (3H, s) |
| 5" | 1.66 (3H, s) |
| 2' | 7.47 (1H, d, J = 2.1 Hz) |
| 5' | 6.83 (1H, d, J = 8.1 Hz) |
| 6' | 7.18 (1H, dd, J = 8.1, 2.1 Hz) |

TABLE II $^{13}$C NMR (75 MHz, CD$_3$OD)
Formula (V)

| | |
|---|---|
| 2 | 147.7 |
| 3 | 184.0 |
| 3a | 104.3 |
| 4 | 156.2 |
| 5 | 111.9 |
| 6 | 167.7 |
| 7 | 91.5 |
| 7a | 166.3 |
| 8 | 112.9 |
| 1' | 125.7 |
| 2' | 118.7 |
| 3' | 146.6 |
| 4' | 148.9 |
| 5' | 116.6 |
| 6' | 125.9 |
| 1" | 22.1 |
| 2" | 123.7 |
| 3" | 131.9 |
| 4" | 25.9 |
| 5" | 17.9 |

TABLE III (Formula VI)
$^1$H NMR (300 MHz, CD$_3$OD) and $^{13}$C NMR (75 MHz, CD$_3$OD)

| | Proton | Carbon |
|---|---|---|
| 2 | | 147.8 |
| 3 | | 183.5 |
| 3a | | 104.5 |
| 4 | | 156.1 |
| 5 | | 111.8 |
| 6 | | 167.6 |
| 7 | 6.27 (s) | 91.5 |
| 7a | | 166.2 |

TABLE III-continued (Formula VI)
$^1$H NMR (300 MHz, CD$_3$OD) and $^{13}$C NMR (75 MHz, CD$_3$OD)

| | Proton | Carbon |
|---|---|---|
| 8 | 6.46 (s) | 111.1 |
| 1' | | 125.6 |
| 2' | 7.96 (s) | 118.7 |
| 3' | | 146.3 |
| 4' | | 148.7 |
| 5' | 6.70 (s) | 120.0 |
| 6' | | 129.3 |
| 1" | 3.23 (m) | 22.1 |
| 2" | 5.17 (br,t) | 123.7 |
| 3" | | 132.0 |
| 4" | 1.64 (s) | 25.9 |
| 5" | 1.74 (s) | 17.8 |
| 2'" | | 147.5 |
| 3'" | | 184.0 |
| 3a'" | | 104.4 |
| 4'" | | 156.8 |
| 5'" | | 111.6 |
| 6'" | | 168.0 |
| 7'" | 6.38 (s) | 92.0 |
| 7a'" | | 168.0 |
| 8'" | 6.62 (s) | 113.1 |
| 1"" | | 125.7 |
| 2"" | 7.21 (dd, 1.8, 8.4 Hz) | 126.0 |
| 3"" | 6.84 (d, 8.4 Hz) | 116.6 |
| 4"" | | 149.0 |
| 5"" | | 146.7 |
| 6"" | 7.52 (d, 1.8 Hz) | 118.7 |

EXAMPLE 15
Preparation of 4,6-dihydroxy-3-benzofuranone

Chloroacetonitrile (4 ml, 63.2 mmol) was added dropwise to a stirred solution containing phloroglucinol dihydrate (10 g, 61.7 mmol) and zinc chloride (8.5 g, 62.4 mmol) in anhydrous ether (100 ml) at room temperature. The resulting solution was then saturated with hydrogen chloride gas. After stirring at room temperature for 24 hours, the orange precipitates were filtered and washed with anhydrous ether (50 ml). The precipitates were then dissolved in water (100 ml) and heated at 100° C. for 1 hr. The solution was allowed to cool to ambient temperature, and aqueous sodium hydroxide (20% w/v) (10 ml) was then added. After stirring at room temperature for an additional 30 minutes, the reaction mixture was acidified by adding dilute hydrochloric acid (1M, 50 ml) and was extracted with ethyl acetate (2×250 ml). The combined organic extracts were washed with brine, dried over magnesium sulfate, filtered and concentrated in vacuo to afford a light orange solid which was then recrystallized from ethyl acetate to give 4,6-dihydroxy-3-benzofuranone as a light orange powder (9.5 g, 93%).

EXAMPLE 16
Preparation of 4,6-dihydroxy-5-prenyl-3-benzofuranone

Aqueous sodium hydroxide (20% w/v)) (10 ml) was added to a stirred solution of 4,6-dihydroxy-3-benzofuranone (3 g, 18.1 mmol) in methanol (50 ml), the reaction mixture immediately turned to a brown color. Prenyl bromide (2.1 ml, 18.2 mmol) in methanol (10 ml) was added dropwise to the solution. After stirring for 30 minutes at room temperature, methanol was removed in vacuo, and ethyl acetate (200 ml) was added to the reaction mixture. The aqueous layer was acidified by adding dilute hydrochloric acid (1M, 50 ml). The organic layer was washed with brine, dried over magnesium sulfate, filtered and concentrated in vacuo to give the crude product mixture as a yellow foam. Silica gel chromatography eluting with a mixture of ethyl acetate and hexanes (1:2), gave 4,6-dihydroxy-5-prenyl-3-benzofuranone (1.25 g, 29.5%), unreacted 4,6-dihydroxy-3-benzofuranone (0.7 g, 23.3%) and a mixture of unidentified products (1.1 g) (could be a mixture of 4,6-dihydroxy-2-prenyl 3-benzofuranone and 4,6-dihydroxy-2,2-diprenyl-3 -benzofuranone).

EXAMPLE 17
Preparation of 4,6-bismethoxymethoxy-5-prenyl-3-benzofuranone

Chloromethyl methyl ether (0.4 ml, 5.27 mmol) was added dropwise to a stirred solution containing 4,6-dihydroxy-5-prenyl-3-benzofuranone (0.5 g, 2.14 mmol) and triethylamine (1 ml) in dimethylformamide (50 ml). After stirring at room temperature for 18 hours, water (100 ml) was added to destroy any excess chloromethyl methyl ether. The reaction mixture was extracted with ethyl acetate (2×250 ml), and the combined organic extracts were washed with brine, dried over magnesium sulfate, filtered and concentrated in vacuo to give a light brown syrup. The crude mixture was chromatographed on silica gel, eluting with a mixture of ethyl acetate and hexanes (1:3), to give 4,6-bismethoxymethoxy-5-prenyl-3-benzofuranone (0.612 g, 88.8%) as a colorless powder.

EXAMPLE 18
Preparation of 3,4-bismethoxymethoxybenzaldehyde

Chloromethyl methyl ether (1.2 ml, 15.8 mmol) was added dropwise to a stirred solution containing 3,4-dihydroxybenzaldehyde (1 g, 7.25 mmol) and triethylamine (2 ml) in dimethylformamide (100 ml). After stirring at room temperature for 2 days, water (100 ml) was added to destroy any excess chloromethyl methyl ether. The reaction mixture was extracted with ethyl acetate (2×250 ml). The combined organic extracts were washed with brine, dried over magnesium sulfate, filtered and concentrated in vacuo to give a brown syrup. The crude mixture was chromatographed on silica gel eluting with a mixture of ethyl acetate and hexanes (1:4) to give first 3,4-bismethoxymethoxybenzaldehyde (0.4 g) as a light yellow syrup, and then the monomethoxymethylated derivatives of 3,4-dihydroxybenzaldehyde.

EXAMPLE 19
Preparation of 5-prenyl-3',4,4',6-tetramethoxymethoxyaurone

Aqueous sodium hydroxide (20% w/v) was added to the stirred solution of 4,6-bismethoxymethoxy-5-prenyl-3-benzofuranone (0.25 g, 0.984 mmol) in methanol (10 ml); the solution turned red. 3,4-Bismethoxymethoxy benzaldehyde (0.22 g, 0.984 mmol) in methanol (10 ml) was then added to the red reaction mixture, and the resulting solution decolorized. After stirring at room temperature for 5 minutes, bright yellow precipitate was formed, and the reaction mixture was allowed to stir for an additional 30 minutes. The bright yellow precipitate was collected and washed with methanol (20 ml) to give 5-prenyl-3',4,4',6-tetramethoxymethoxy-aurone as a bright yellow powder (0.37 g, 78.7%).

EXAMPLE 20
Preparation of 5-prenylaureusidin

Trimethylsilyl chloride (0.2 ml) was added to a suspension of 5-prenyl-3',4,4',6-tetramethoxymethoxyaurone (10 mg) in methanol (5 ml). After stirring for 18 hours at room temperature, the reaction mixture was partitioned between ethyl acetate (50 ml) and water (25 ml). The organic extracts were washed with brine, dried over magnesium sulfate, filtered, and concentrated in vacuo to give a brown foam. The crude product was purified by reversed phase HPLC to give 5-prenylaureusidin (4 mg) as a brown powder. Washing with 1 M HCl can cause cyclization of the isopentenyl group with the adjacent phenol to form a pyran, as evidenced by the movement of the methyl signal to the 6 1.4 region in the $^1$H NMR spectrum of the crude product.

EXAMPLE 21
Inhibition of Candida spp. culture

*Candida albicans* (strain ATCC #90028), *Candida krusei* (strain ATCC #90030), and *Torulopsis* (Candida) *glabrata* (strain ATCC #6258) were subcultured from cryopreserved stocks onto sabourand dextrose agar plates. Blastoconidia were suspended into RPMI-MOPS (media) and inoculated (500 cfu/well) into 96-well plates containing test compounds in a final volume of 100 μL/well. After 22 hours at 35° C., 25 μL of XTT (2,3-bis(2-methoxy-4-nitro-5-sulfophenyl)-5-[(phenylamino)carbonyl] -2H-tetrazolium hydroxide), (100 μg/mL) with PMS (phenazine methyl sulfate, 5 μM) were added to each well, followed by 2 hours of shaking. Growth was assessed spectrophotometrically by measuring the appearance of soluble formazan stain at 450 nm using an $E_{max}$ microplate reader. Validity of the assay was confirmed by determination of the *C. albicans* minimum inhibitory concentration (MIC) for known antifungal agents such as amphotericin B, 5-flucytosine, fluconazole, nikkomycin Z, and polyoxin D, which were found to be within reported ranges. The antifungal MIC of formula (V) for *C. albicans*, *C. krusei*, and *T. glabrata*, respectively, were 12.5 μg/mL, 6.25 μg/mL, and 6.25 μg/mL. The antifungal MIC of formula (VI) was 25 μg/mL, 7.48 μg/mL, and 1.74 μg/mL for *C. albicans*, *C. krusei*, and *T.* (C.) *glabrata*, respectively.

EXAMPLE 22
Inhibition of Chitin Synthases

Chitin synthases are attractive antifungal targets because, while critical to fungal cell growth and function, there are no known chitin synthase enzymes in mammalian cells. Chitin synthase III is required for the synthesis of about 90% of yeast cell chitin, particularly the chitin found in bud scars and lateral cell walls. Chitin synthases I and II together are responsible for only a small remainder of cellular chitin production. Chitin synthase I is required for normal budding in acidic media, while chitin synthase II is required for normal morphology, septation, and cell separation (*Ann. Rev. Microbiol.* 1993, 47:505–534).

The simultaneous loss (double mutation) of chitin synthases II and III, with or without loss of chitin synthase I, is lethal. This accounts for the antifungal activity of known chitin synthase inhibitors (McCullough, J. E. "Importance of Chitin Synthesis for Fungal Growth and as a Target for Antifungal Agents" in *New Approaches for Antifungal Drugs* edited by P. B. Feurander, Birkhauser, Boston Mass., 1992, pp 32–45).

Combined Inhibition of Chitin Synthase (CS) II and III

Plasma membrane was purified from *C. albicans* (ATCC #90028) according to Orlean, *J. Biol. Chem.* 262:5732–5739 1987. To minimize proteolysis during plasma membrane preparation, 1% fetal calf serum was incorporated into the homogenization buffer. Plasma membrane was activated by trypsin (125 μg/mg protein) in the presence of 1.5 mM UDP-GLcNAc(c) at 25° C. for 5 minutes. The reaction was stopped by the addition of soybean trypsin inhibitor. The activated membranes (0.125 mg membrane protein/mL) were then assayed in a total of 50 μL reaction mixture containing 50 mM Tris-HCl (pH 8.0) 3 mM $CoCl_2$, 40 mM GlcNAc, 4 mM $^{14}$C-UDP-GlcNAc (specific: 0.25 mCi/mmol) (New England Nuclear, Boston, Mass.) and plant extract (100 μg/mL). The incubation was carried out at 37° C. for 1 hour and terminated with the addition of trichloroacetic acid (10%). The reaction mixture was transferred to a pre-wetted glass fiber filter. The filter was washed with 4×200 μL of a 7:3 solution of 95% EtOH and 1 M acetic acid. The filter was dried under a heat lamp and counted in a Microbeta counter (Wallac, Gaithersburg, Md.) after the addition of 25 4L OPTIPHASE SUPERMIX™ (Wallac) scintillation fluid. Nikkomycin Z and Polyoxin D were used as positive controls (Calbiochem, San Diego, Calif.). Vehicle control was carried out with the same amount of DMSO (2%).

Measurement of CS II Inhibition Only

The SOP assay described above was modified to pH 7.5 and 5 mM $MgCl_2$ (instead of $CoCl_2$). In addition, twice as much membrane protein was used per reaction, and 10 μM Nikkomycin Z was added. Results demonstrated that CS II was much more resistant to Nikkomycin Z than either CS I or CS III and represented the major isozyme measured (75% of the CS II remained).

Measurement of CS III Inhibition Only

Conditions for the SOP assay were followed except that the membrane was not activated by trypsin, and twice as much membrane protein was used per reaction. CS III is the only isozyme that does not require trypsin activation and is the only one measured under these conditions in Orlean. The $K_m$ for UDP-GlcNAc and $K_i$ for Nikkomycin Z were determined using the SOP assay conditions (pH 8, 3.0 mM $Co^{+2}$) plus 30 μM Polyoxin D, which inhibits any residual CS I. The experimental values for $K_m$ UDP-GlcNAc for CS II and CS III, and the experimental values for $K_i$ Nikkomycin Z for CS II were within less than one order of magnitude of the reported values (no reported value of $K_i$ for CS III).

Choi and Cabib, *Anal. Biochem.* 219:368–372 (1994), used pH 8.0 and 3.0 mM $Co^{+2}$ to select for CS II and CS III in wild type *Saccharomyces cerevisiae*. Both CS II and CS III were present when the membrane preparation was treated with trypsin; however, only CS III was present when the membrane was not treated with trypsin. These conditions virtually eliminated CS I. The distribution of chitin synthase between CS II and CS III at pH 8.0, 3.0 mM $Co^{+2}$ was similar to the reported values for *C. albicans* (within 10%).

The criterion for the initial screening was 50% inhibition. This criterion and enzyme distribution allowed identification of selective CS II only inhibitors, but would not identify CS III only inhibitors. Follow-up testing identified the relative distribution of the inhibition against CS II or CS III, insuring that inhibitors against both enzymes were selected. The follow-up testing criteria was the sum of inhibition for both CSII and CSIII, which was preferably at least 50%.

The compound of formula (V) demonstrated inhibition toward chitin synthases ($IC_{50}$ of 223 μM for CS II and 107 μM for CS III).

EXAMPLE 23
Inhibition of Glucan Synthase

Plasma membranes were purified from *C. albicans* according to Tang et al. *Antimicrob. Agents Chemother.* 35:99–103 (1991). 6.25 μg of membranes (i.e. of membrane protein) were incubated in 2 mM $^{14}$C-UDPGlucose (specific: 0.25 mCi/mmol), 50 μg of amylase, 25 keg of bovine serum albumin, dithiothreitol (DTT) (1 mM), EDTA (5 mM), KF (10 mM), GTP-γ-S (100 μM) sucrose (1 M), and 50 mM Tris-HCl (pH 8.0) in a volume of 100 μL. The mixture was incubated at 27° C. for one hour and the reaction was terminated by the addition of TCA at a final concentration of 10%. The $^{14}$C-labelled glucan was harvested and counted as described above for chitin synthase. Pneumocandin B was used as a positive control. The compound of formula (V) inhibited glucan synthase with an $IC_{50}$ of 246 μM. Inhibitors of glucan synthase and chitin synthase are known to have synergistic effects against C. albicans growth. Compound (V) may be a dual-acting antifungal agent.

EXAMPLE 24
Inhibition of Fluconazole-resistant and Fluconazole-sensitive Candidiasis in Mice Immunocompetent mice (ICR, Sprague-Dawley, Indianapolis, IN) were infected with a pathogenic strain (strain # 64) of Candida albicans which is sensitive to fluconazole. After 24 hours, dissemination of infection was shown by organ colony counts (kidney, spleen, and liver) greater than 105 colony forming units (CFU). Treatment began 24 hours after infection with the indicated dosage once a day for 10 days. All of the untreated control mice died after about 16 days. After 30 days the percent survival in the group treated with fluconazole (40 mg per kg body weight, twice a day) was about 30%. In contrast, the percent survival in the test group treated with Formula (V) (40 mg per kg body weight administered p.o.) was about 60%, and the percent survival in the test group treated with Formula (V) (20 mg per kg body weight administered i.p.) was about 70%. In addition, the organ fungal load (in CFU) was measured at day 30. The groups treated with formula (V) had between 3% and 10% of the fungal load in the same organ of the fluconazole-treated group. In other words, the fungal load reduction in the formula (V) groups was, in each organ, over 99%, whereas the reduction in the fluconazole group was between 94.3% and 95.3%.

In a similar experiment using a fluconazole-resistant clinical isolate (C. albicans UTR-14, provided by Alan Sugar, Boston University, Boston, Mass.), the percent survival after 20 days of the group treated with formula (V) at a dosage of 40 mg per kg body weight p.o. was about 80%. The percent survival in the group treated with fluconazole (40 mg per kg body weight p.o. (twice daily)) and in the untreated group was 0% in each case.

These data demonstrated the surprising efficacy of the disclosed compounds, represented by formula (V), against fluconazole-resistant and fluconazole-sensitive strains of Candida albicans.

EXAMPLE 25
Inhibition of C. albicans with Drug Combinations

Formula (V) was tested in combination with known antifungal agents amphotericin B and fluconazole. A 10 mg/ml stock solution of formula (V) was diluted in 100% DMSO and stored at –80° C. Fluconazole and Amphotericin B were similarly prepared and stored as a 8 mg/ml stock solution, and a 1.25 mg/ml stock solution, respectively. Each known antifungal agent was added (2 μl/well), then 2 μl/well of the formula (V) solution was added to the designated wells. The remainder of the experiment follows Example 21. The results demonstrated apparent additivity with fluconazole and apparent synergy with Amphotericin B.

Scheme P-1 shows several compounds of the invention.

Scheme P-1

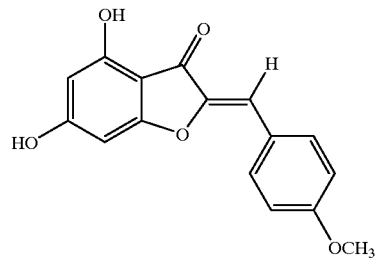

S01

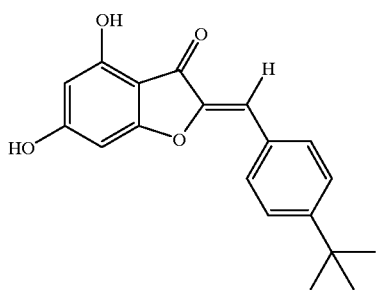

S02

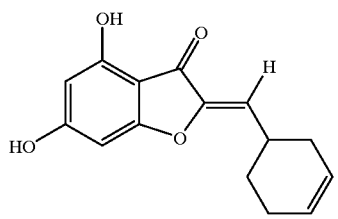

S03

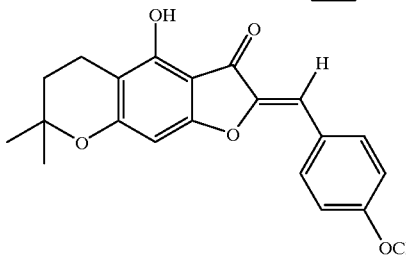

S04

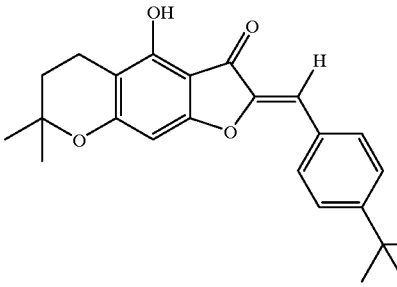

S05

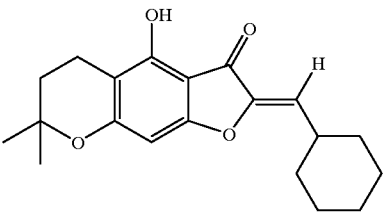

S06

-continued
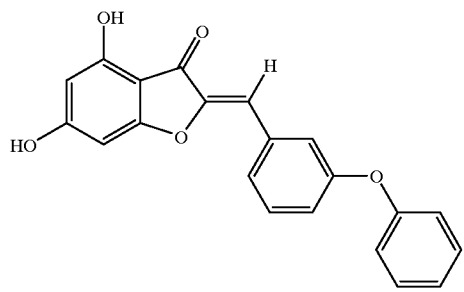
S08
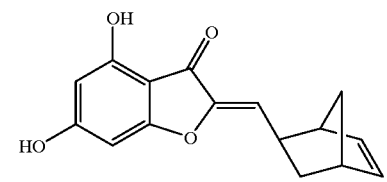
S09
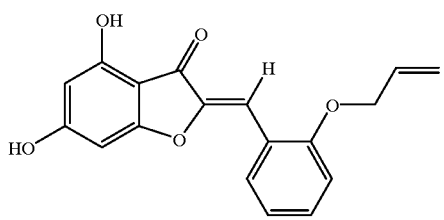
S10
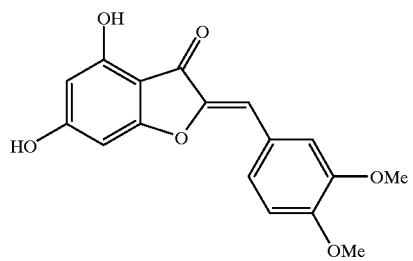
S11
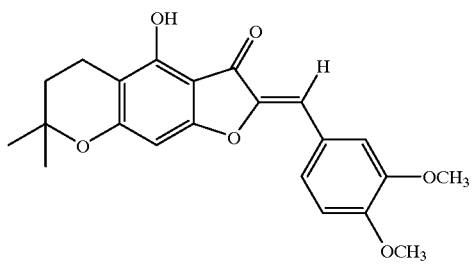
S12
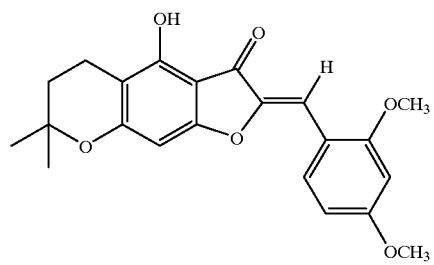
S13
-continued
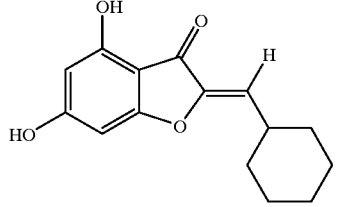
S14
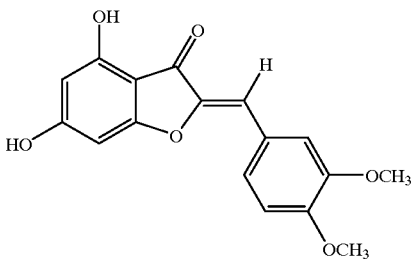
S15
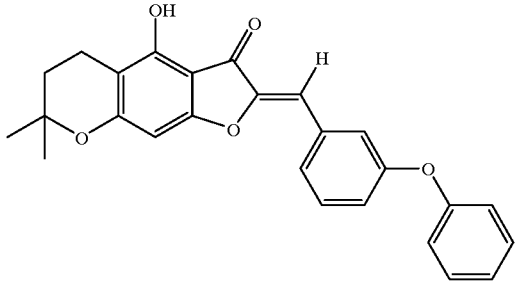
S16
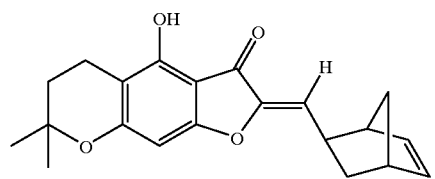
S17
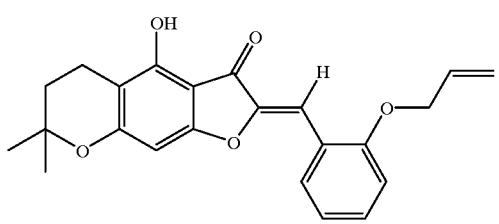
S18
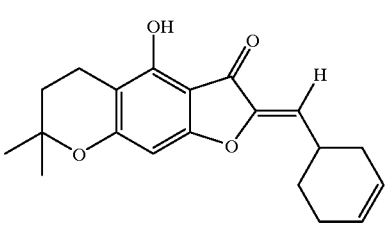
S19
All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A compound having the formula (III):

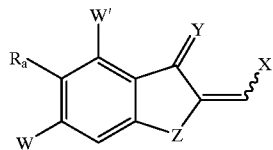

wherein
W is selected from the group consisting of H, OH, Br, Cl, I, amino, thiol, cyano, nitro, $C_{1-4}$ alkoxy, $C_{1-4}$ alkenyloxy, $C_{2-6}$ alkyloxyalkyleneoxy, $C_{2-7}$ carboxyalkyloxy, $C_{7-15}$ arylalkoxy, and $C_{1-4}$ alkylthio;
W' is hydroxyl;
$R_a$ is selected from the group consisting of H, $C_{3-18}$ alkyl, $C_{3-18}$ alkenyl, $C_{5-18}$ cyclohexenyl, and $C_{6-18}$ aryl;
X is substituted or unsubstituted $C_{3-15}$ alkyl, $C_{3-18}$ alkenyl, $C_{3-15}$ cycloalkyl, $C_{4-15}$ cycloalkenyl, $C_{4-20}$ bicyclo(a.b.c)alkyl, $C_{5-20}$ bicyclo(a.b.c) alkenyl, $C_{8-20}$ tricyclo(a.b.c.d)alkyl, $C_{8-20}$ tricycloalkenyl, and $C_{2-20}$ heterobicyclo(a.b.c)alkyl, wherein each of a, b, c, and d is independently 0 to 10; and
each of Y and Z is 0.

2. The compound of claim 1, wherein X is selected from the group consisting of $C_{3-15}$ alkyl, $C_{3-18}$ alkenyl, $C_{3-15}$ cycloalkyl, $C_{4-15}$ cycloalkenyl, $C_{5-10}$ bicyclo(a.b.c)alkyl, $C_{5-10}$ bicyclo(a.b.c)alkenyl, $C_{8-20}$ tricyclo(a.b.c.d)alkyl, $C_{8-20}$ tricycloalkenyl, and $C_{3-10}$ heterobicyclo(a.b.c)alkyl, wherein each of a, b, c, and d is independently 0 to 6.

3. The compound of claim 2, wherein X is selected from the group consisting of $C_{3-15}$ alkyl, $C_{3-18}$ alkenyl, $C_{3-15}$ cycloalkyl, and $C_{4-15}$ cycloalkenyl.

4. The compound of claim 2, wherein X is selected from the group consisting of $C_{5-10}$ bicyclo(a.b.c.)alkyl, $C_{5-10}$ bicyclo(a.b.c)alkenyl, $C_{8-15}$ tricyclo(a.b.c.d)alkyl, $C_{8-15}$ tricycloalkenyl, and $C_{3-10}$ heterobicyclo(a.b.c)alkyl, wherein each of a, b, c, and d is independently 0 to 6.

5. The compound of claim 2, wherein W is selected from the group consisting of H, hydroxyl, methoxy, hydroxymethyl, and halomethyl.

6. The compound of claim 2, wherein W is hydroxyl.

* * * * *